United States Patent
Aoki et al.

(10) Patent No.: US 10,712,323 B2
(45) Date of Patent: Jul. 14, 2020

(54) CONTROL DEVICE FOR GAS DETECTOR AND CONTROL METHOD FOR GAS DETECTOR

(71) Applicant: Toyota Jidosha Kabushiki Kaisha, Toyota-shi, Aichi-ken (JP)

(72) Inventors: Keiichiro Aoki, Shizuoka-ken (JP); Keigo Mizutani, Okazaki (JP); Kazuhiro Wakao, Susono (JP); Kazuhisa Matsuda, Susono (JP)

(73) Assignee: Toyota Jidosha Kabushiki Kaisha, Toyota-shi, Aichi-ken (JP)

( * ) Notice: Subject to any disclaimer, the term of this patent is extended or adjusted under 35 U.S.C. 154(b) by 394 days.

(21) Appl. No.: 15/796,219

(22) Filed: Oct. 27, 2017

(65) Prior Publication Data

US 2018/0149631 A1  May 31, 2018

(30) Foreign Application Priority Data

Nov. 30, 2016 (JP) .................. 2016-233376

(51) Int. Cl.
*G01N 27/407* (2006.01)
*G01N 33/00* (2006.01)
*F02D 41/14* (2006.01)

(52) U.S. Cl.
CPC ..... *G01N 33/0042* (2013.01); *F02D 41/1444* (2013.01); *F02D 41/1454* (2013.01);
(Continued)

(58) Field of Classification Search
CPC ............. G01N 27/407; G01N 27/4074; G01N 27/4065; F01N 2560/027
See application file for complete search history.

(56) References Cited

U.S. PATENT DOCUMENTS

| 6,083,370 | A | 7/2000 | Kato et al. |
| 2002/0043460 | A1 | 4/2002 | Ikeda |

(Continued)

FOREIGN PATENT DOCUMENTS

| CN | 105675691 A | 6/2016 |
| JP | H10232220 A | 9/1998 |

(Continued)

OTHER PUBLICATIONS

JPO computer-generated English language translation of the Description section of Japanese application JP 2013-009255 (Year: 2013).*

(Continued)

*Primary Examiner* — Alexander S Noguerola
(74) *Attorney, Agent, or Firm* — Dinsmore & Shohl LLP

(57) ABSTRACT

An electronic central unit is configured to control a voltage application device to execute applied voltage sweep and obtain an output current that flows between a first electrode and a second electrode of an electrochemical cell. The electronic control unit is configured to detect either one of presence or absence of sulfur oxides in a specified concentration or higher in exhaust gas and a concentration of sulfur oxides in the exhaust gas based on the output current. The electronic control unit is configured to execute one of a specified determination and a specified detection based on a specified parameter. Accordingly, it is possible to accurately determine the presence or the absence of sulfur oxides in the specified concentration or higher that are contained in exhaust gas or detect the concentration of sulfur oxides in the exhaust gas.

18 Claims, 11 Drawing Sheets

(52) U.S. Cl.
CPC ..... *G01N 27/4074* (2013.01); *F02D 2250/14* (2013.01); *Y02A 50/248* (2018.01)

(56) References Cited

U.S. PATENT DOCUMENTS

2006/0236677 A1* 10/2006 Inagaki ................. F02D 41/146
                                                             60/276
2018/0149618 A1    5/2018  Wakao et al.

FOREIGN PATENT DOCUMENTS

| JP | 2002-071633 A | | 3/2002 | |
| --- | --- | --- | --- | --- |
| JP | 2009-053108 A | | 3/2009 | |
| JP | 2014-142199 | * | 8/2014 | ............ G01N 27/46 |
| JP | 2015-017931 A | | 1/2015 | |
| JP | 2015-155665 A | | 8/2015 | |
| WO | 2015/124992 A1 | | 8/2015 | |
| WO | 2015124985 A1 | | 8/2015 | |

OTHER PUBLICATIONS

Notice of Allowance issued to U.S. Appl. No. 15/796,240 dated Jan. 31, 2020.
U.S. Appl. No. 15/796,240, filed Oct. 27, 2017; Inventors: Kazuhiro Wakao et al.
Office Action dated Oct. 22, 2019 in U.S. Appl. No. 15/796,240.

* cited by examiner

CONTROL DEVICE FOR GAS DETECTOR AND CONTROL METHOD FOR GAS DETECTOR

CROSS-REFERENCE TO RELATED APPLICATIONS

This application claims priority to Japanese Patent Application No. 2016-233376 filed on Nov. 30, 2016, which is incorporated herein by reference in its entirety including the specification, drawings and abstract.

BACKGROUND

1. Technical Field

The disclosure relates to a control device for a gas detector that determines whether sulfur oxides in a specified concentration or higher are contained in exhaust gas (detected gas) of an internal combustion engine or that detects the concentration of the sulfur oxides contained m the exhaust gas, and to a control method for a gas detector.

2. Description of Related Art

In order to control an internal combustion engine, an air-fuel ratio sensor (hereinafter referred to as an A/F sensor) that obtains an air-fuel ratio (A/F) of air mixture in a combustion chamber on the basis of a concentration of oxygen ($O_2$) contained in exhaust gas has been widely used. One type of such an air-fuel ratio sensor is a limiting current type gas sensor.

Furthermore, a SOx concentration detector (hereinafter referred to as a conventional device) that detects a concentration of sulfur oxides (hereinafter referred to as SOx) in the exhaust gas by using such a limiting current type gas sensor has been proposed (for example, see Japanese Patent Application Publication No. 2015-17931 (JP 2015-17931 A)).

The conventional device includes a pump cell (an electrochemical cell) that uses an oxygen pumping effect of an oxygen ion conductive solid electrolyte. The conventional device applies a voltage to paired electrodes of the pump cell to resolve gas components including oxygen atoms in the exhaust gas (for example, $O_2$, SOx, $H_2O$, and the like, and hereinafter will also be referred to as oxygen containing components), and thereby generates oxide ions ($O^{2-}$). The conventional device detects a characteristic of the current flowing between the electrodes when the oxide ions, which are generated through decomposition of the oxygen containing components, move between the electrodes of the pump cell (the oxygen pumping effect).

More specifically, the conventional device executes applied voltage sweep when detecting the SOx concentration. That is, after boosting an applied voltage applied to the pump cell from 0.4 V to 0.8 V, the conventional device executes the applied voltage sweep to lower the applied voltage from 0.8 V to 0.4 V.

Then, the conventional device computes the SOx concentration by using a difference between a current (hereinafter referred to as an output current) flowing through the electrodes of the pump cell at a time point at which the applied voltage reaches 0.8 V and a peak value as the smallest value of the output current during the period in a direction where the applied voltage is lowered from 0.8 V to 0.4 V.

SUMMARY

However, there is s high possibility that the above output current is changed due to an influence of the oxygen containing components other than SOx contained in the exhaust gas. For example, a decomposition voltage of water ($H_2O$) is approximately the same as or slightly higher than a decomposition voltage of sulfur oxides. Furthermore, a concentration of water in the exhaust gas fluctuates is accordance with the air-fuel ratio of the air mixture. For this reason, it is difficult to eliminate the influence on the output current resulted from the decomposition of water and to detect the output current only resulted from the decomposition of SOx components. Accordingly, it has been desired to determine whether sulfur oxides in a specified concentration or higher exist in the exhaust gas or to detect the concentration of sulfur oxides in the exhaust gas by using a change in the output current that is not influenced by the oxygen containing components other than SOx and is only resulted from the SOx components.

The disclosure accurately determines whether sulfur oxides in a specified concentration or higher are contained in exhaust gas, or accurately detects concentration of sulfur oxides.

A first aspect of the disclosure is a control device for a gas detector. The gas detector includes an element section, a voltage application device, a current detector, and an electronic control unit. The element section includes an electrochemical cell and a diffusion resistance body and is provided in an exhaust passage of an internal combustion engine. The electrochemical cell includes a solid electrolyte body that has oxide ion conductivity, a first electrode and a second electrode, the first electrode and the second electrode being respectively provided on surfaces of a solid electrolyte body. The diffusion resistance body is constituted a porous material through which exhaust gas flowing through the exhaust passage is passable. The element section is configured that the exhaust gas flowing through the exhaust passage reaches the first electrode through the diffusion resistance body. The voltage application device is configured to apply a voltage between the first electrode and the second electrode. The current detector is configured to detect an output current that is a current flowing between the first electrode and the second electrode. The electronic control unit is configured to control an applied voltage that is the voltage applied between the first electrode and the second electrode by using the voltage application device. The electronic control unit is configured to obtain the output current by using the current detector. The electronic control unit is configured to execute lowering sweep after executing boosting sweep by using the voltage application device when the electronic control unit determines that an air-fuel ratio of air mixture supplied to the internal combustion engines in a stable state. The boosting sweep is control to boost the applied voltage from a first voltage to a second voltage, the first voltage is selected from a first voltage range that is lower than a decomposition initiation voltage of sulfur oxides, and the second voltage is selected from a second voltage range that is higher than the decomposition initiation voltage of sulfur oxides. The lowering sweep is control to lower the applied voltage from the second voltage to the first voltage at a specified lowering rate. The electronic control unit is configured to obtain a specified parameter based on the output current and execute one of a specified determination and a specified detection based on the specified parameter. The specified determination is a determination on whether sulfur oxides in a specified concentration or higher are contained in the exhaust gas. The specified detection is detection of a concentration of the sulfur oxides in the exhaust gas. The specified parameter is a specified change, and correlated with a change occurred to the output current, the output current is increased as the concentration of the sulfur oxides contained in the exhaust gas is increased. The specified change is a change occurred to the output current due to the current flowing between the first electrode and the second electrode at a time when a reoxidation reaction of specified sulfur in the first electrode leads to generation of sulfur oxides. The specified sulfur is sulfur that is adsorbed to the first electrode at a time when the applied voltage becomes lower than the decomposition initiation voltage of sulfur oxides during the lowering sweep. The specified lowering rate is set to such a rate that a rate of the reoxidation reaction of the specified sulfur is rapidly increased at a time point at which the applied voltage becomes a voltage that fells within the first voltage range and also falls within a higher voltage range than the first voltage.

With the configuration, the lowering rate in the lowering sweep by the gas detector is set to such a rate that the rate of the reoxidation reaction of sulfur is rapidly increased at the time point at which the applied voltage becomes the voltage that falls within the first voltage range (the voltage range that is lower than the decomposition initiation voltage of sulfur oxides) and that falls within a higher voltage range than the first voltage. Accordingly, the change in the output current that is not influenced by oxygen containing components other than sulfur oxides appears significantly as the concentration of sulfur oxides is increased. Furthermore, the gas detector obtains the parameter that is correlated with the change occurred to the output current due to the reoxidation reaction of sulfur based on the output current. Then, the gas detector is configured to execute one of the specified determination and the specified detection based on the parameter. Therefore, it is possible to accurately determine presence or absence of sulfur oxides in the specified concentration or higher that are contained in exhaust gas or detect the concentration of sulfur oxides in the exhaust gas.

In the control device for the gas detector, the electronic control unit may be configured to store the output current at a time point that an applied voltage becomes a reoxidation current detection voltage during the lowering sweep as a base current in advance. The reoxidation current detection voltage may be a voltage that falls within the first voltage range and is higher than the first voltage. The electronic control unit may be configured to make the exhaust gas as detected gas that does not contain sulfur oxides flow through the exhaust passage and to execute the boosting sweep and the lowering sweep. The electronic control unit may be configured to compute a difference between the base current and the output current, and may be configured to use the difference as the parameter, the output current is a current that is obtained at the time point that the applied voltage becomes the reoxidation current detection voltage during the lowering sweep.

With the configuration, the difference that accurately indicates the concentration of sulfur oxides is used to determine whether sulfur oxides in the specified concentration or higher are contained in the exhaust gas or to detect the concentration of sulfur oxides in the exhaust gas. Thus, such a determination or such detection can further accurately be made.

In the control device for the gas detector, the electronic control unit may determine whether a magnitude of the difference is equal to or larger than a threshold difference. The electronic control unit may determine that sulfur oxides in the specified concentration or higher are contained in the exhaust gas when the electronic control unit determines that the magnitude of the difference is equal to or larger than the threshold difference. The electronic control unit may be configured to determine that sulfur oxides in the specified concentration or higher are not contained in the exhaust gas when the electronic control unit determines that the magnitude of the difference is smaller than the threshold difference.

With the configuration, it is determined whether the magnitude of the difference, which accurately indicates the concentration of sulfur oxides, is equal to or larger than the threshold difference corresponding to the specified concentration. In this way, it is possible to accurately determine whether sulfur oxides in the specified concentration or higher are contained in the exhaust gas.

In the control device for the gas detector, the electronic control unit may be configured to store a relationship between the difference and a concentration of sulfur oxides in the exhaust gas. The electronic control unit may configured to detect the concentration of sulfur oxides in the exhaust gas based on the difference and the relationship.

With the configuration, the concentration of sulfur oxides in the exhaust gas is detected based on the difference, which accurately indicates the concentration of sulfur oxides, and the above relationship. Therefore, the concentration of sulfur oxides in the exhaust gas can accurately be detected.

In the control device for the gas detector, the electronic control unit may be configured to compute a minimum change amount and may be configured to use the minimum change amount as the parameter. The minimum change amount may be a minimum value of a change amount of the output current which is obtained by the electronic control unit, per specified elapsed time in a period in which the applied voltage falls within the first voltage range during the lowering sweep.

With the configuration, the reoxidation current change becomes significant as the concentration of sulfur oxides contained in the exhaust gas is increased. Accordingly, as the concentration of sulfur oxides contained in the exhaust gas is increased, a magnitude of a changing rate (a lowering rate) of the output current during the lowering sweep is increased. Therefore, the minimum value of the change amount of the output current per specified elapsed time (that is, the minimum change amount) that is obtained as the parameter representing the degree of the reoxidation current change in the above aspect accurately Indicates the concentration of sulfur oxides. Then, according to the configuration, by using this minimum change amount, it is determined whether sulfur oxides in the specified concentration or higher are contained in the exhaust gas, or the concentration of sulfur oxides in the exhaust gas is detected. Thus, such a determination or such detection of the concentration can accurately be made.

In the control device for the gas detector, the electronic control unit may determine whether a magnitude of the minimum change amount is equal to or larger than a threshold minimum change amount. The electronic control unit may be configured to determine that sulfur oxides in the specified concentration or higher are contained in the exhaust gas when the electronic control unit determines that the magnitude of the minimum change amount is equal to or larger than the threshold minimum change amount. The electronic control unit may be configured to determine that sulfur oxides in the specified concentration or higher are not contained in the exhaust gas when the electronic control unit determines that the magnitude of the minimum change amount is smaller than the threshold minimum change amount.

With the configuration, it is determined whether the magnitude of the minimum change amount that accurately indicates the concentration of sulfur oxides is equal to or larger than the threshold minimum change amount. In this way, the determination on whether sulfur oxides in the specified concentration or higher are contained in the exhaust gas is made. Therefore, it is possible to accurately determine whether sulfur oxides in the specified concentration or higher are contained in the exhaust gas.

In the control device for the gas detector, the electronic control unit may be configured to store a relationship between the minimum change amount and a concentration of sulfur oxides in the exhaust gas and may detect the concentration of sulfur oxides in the exhaust gas based on the minimum change amount and the relationship.

With the configuration, the concentration of sulfur oxides in the exhaust gas is detected based on the above minimum change amount, which accurately indicates the concentration of sulfur oxides, and the above relationship. Therefore, the concentration of sulfur oxides in the exhaust gas can accurately be detected.

In the control device for the gas detector, the electronic control unit may be configured to set the applied voltage to an air-fuel ratio applied voltage by using the voltage application device before executing one of the specified determination and the specified detection. The air-fuel ratio applied voltage may be the applied voltage that is selected from a range where a limiting current of oxygen is generated. The electronic control unit may be configured to obtain the output current when the applied voltage is set as the air-fuel ratio applied voltage and to determine the first voltage and the second voltage based on one of an oxygen concentration in the exhaust gas and the air-fuel ratio of the air mixture supplied to the engine. The oxygen concentration may be estimated based on the output current. The air-fuel ratio of the air mixture may be estimated based on the output current.

With the configuration, it is possible to avoid the detection of the output current, which is used for the determination or the detection of the concentration described above in the case where the voltage in the applied voltage sweep falls within an internal resistance dependent region in which the upper limit voltage is boosted as the air-fuel ratio of the internal combustion engine becomes leaner. In other words, the first voltage can be set to a voltage that is higher than that within the internal resistance dependent region, and in conjunction with this, the second voltage can also be set to an appropriate value. Accordingly, it is possible to accurately determine whether sulfur oxides in the specified concentration or higher are contained in exhaust gas or detect the concentration of sulfur oxides in the exhaust gas.

A second aspect of the disclosure is a control method for a gas detector. The gas detector includes an element section, a voltage application device, a current detector, and an electronic control unit. The element section includes an electrochemical cell and a diffusion resistance body and is provided in an exhaust passage of an internal combustion engine. The electrochemical cell includes a solid electrolyte body that has oxide ion conductivity, a first electrode and a second electrode, the first electrode and the second electrode being respectively provided on surfaces of a solid electrolyte body. The diffusion resistance body is constituted a porous material through which exhaust gas flowing through the exhaust passage is passable. The element section is configured that the exhaust gas flowing through the exhaust passage reaches the first electrode through the diffusion resistance body. The voltage application device is configured to apply a voltage between the first electrode and the second electrode. The current detector is configured to detect an output current that is a current flowing between the first electrode and the second electrode. The control method includes: controlling, by the electronic control unit, an applied voltage that is the voltage is applied between the first electrode and the second electrode using the voltage application device; obtaining, by the electronic control unit, the output current using the current detector; executing, by the electronic control unit, lowering sweep after executing boosting sweep using the voltage application device when the electronic control unit determines that an air-fuel ratio of air mixture supplied to the internal combustion engine is in a stable state; and obtaining, by the electronic control unit, a specified parameter based on the output current and executing, by the electronic control unit, one of a specified determination and specified detection based on the specified parameter. The boosting sweep is control to gradually boost the applied voltage from the first voltage to the second voltage. The first voltage is selected from a first voltage range that is lower than a decomposition initiation voltage of sulfur oxides, and the second voltage is selected from a second voltage range that is higher than the decomposition initiation voltage of sulfur oxides. The lowering sweep is control to lower the applied voltage from the second voltage to the first voltage at a specified lowering rate. The specified determination is a determination on whether sulfur oxides in a specified concentration or higher are contained in the exhaust gas. The specified detection is detection of a concentration of the sulfur oxides in the exhaust gas. The specified parameter is a specified change and correlated with a change occurred to the output current. The output current is increased as the concentration of the sulfur oxides contained in the exhaust gas is increased. The specified change is a change occurred to the output current due to the current flowing between the first electrode and the second electrode at a time when a reoxidation reaction of specified sulfur in the first electrode leads to generation of sulfur oxides. The specified sulfur is sulfur that is adsorbed to the first electrode at a time when the applied voltage becomes lower than the decomposition initiation voltage of sulfur oxides during the lowering sweep. The specified lowering rate is set to such a rate that a rate of the reoxidation reaction of the specified sulfur is rapidly increased at a time point at which the applied voltage becomes a voltage that falls within the first voltage range and also falls within a higher voltage range than the first voltage.

With the configuration, the lowering rate in the lowering sweep by the gas detector is set to such a rate that the rate of the reoxidation reaction of sulfur is rapidly increased at the time point at which the applied voltage becomes the voltage that falls within the first voltage range (the voltage range that is lower than the decomposition initiation voltage of sulfur oxides) and that falls within a higher voltage range than the first voltage. Accordingly, the change in the output current that is not influenced by oxygen containing components other than sulfur oxides appears significantly as the concentration of sulfur oxides is increased. Furthermore, the gas detector obtains the parameter that is correlated with a degree of the change occurred to the output current due to the reoxidation reaction of sulfur based on the output current. Then, the gas detector is configured to make either one of the specified determination and the specified detection based on the parameter. Therefore, it is possible to accurately determine presence or absence of sulfur oxides in the specified concentration or higher that is contained in exhaust gas or detect the concentration of sulfur oxides in the exhaust gas.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

Figure 1:
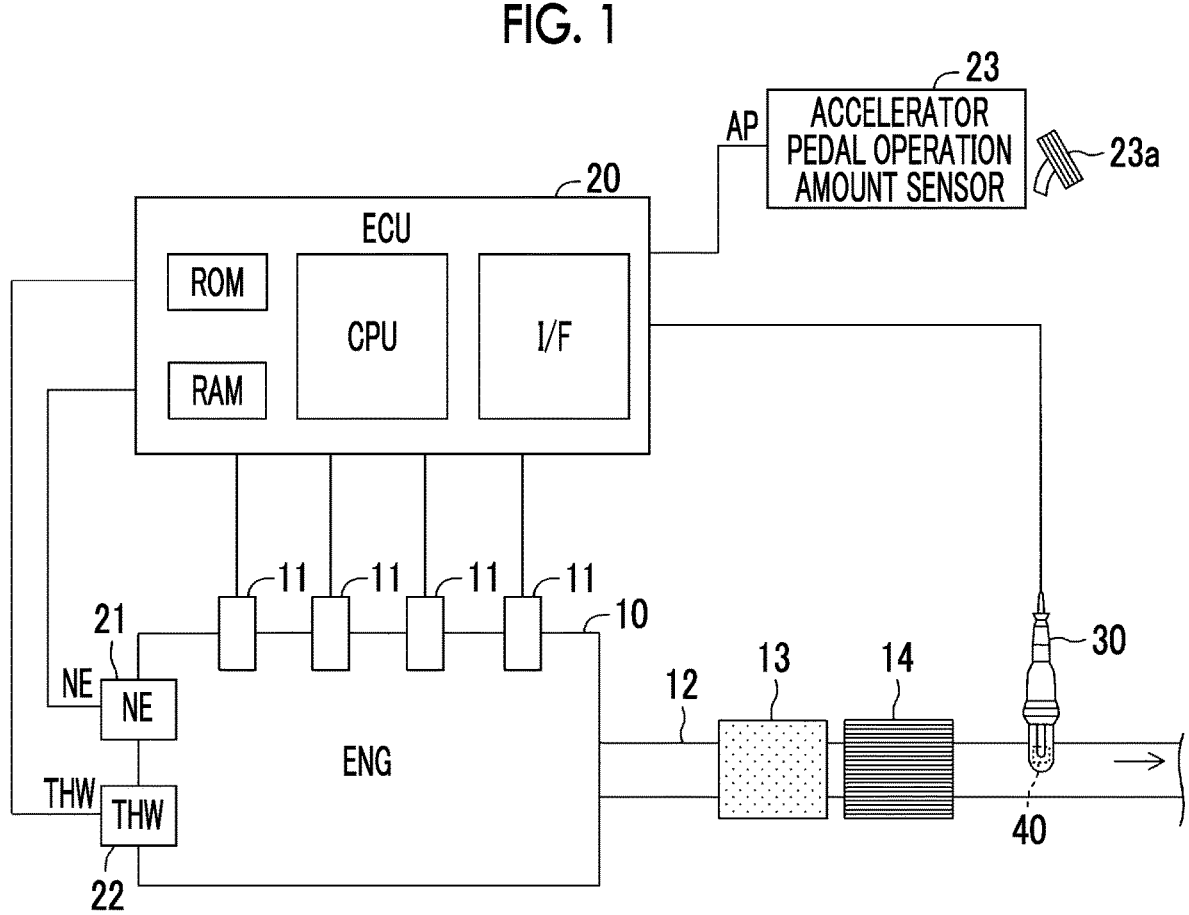
FIG. 1 is a schematic configuration diagram of a gas detector according to a first embodiment of the disclosure and an internal combustion engine, to which the gas detector is applied.

A description will hereinafter be made on a gas detector according to each embodiment of the disclosure with reference to the drawings. Note that the same or corresponding portions in all of the drawings of the embodiments are denoted by the same reference numerals.

A description will be made on the gas detector according to a first embodiment of the disclosure (hereinafter referred to as a first detector). The first detector is applied to an internal combustion engine 10 shown in FIG. 1 that is mounted on a vehicle, which is not shown.

The internal combustion engine 10 is a well-known diesel engine. The internal combustion engine 10 includes a combustion chamber, which is not shown, and a fuel injection valve 11. The fuel injection valve 11 is disposed in a cylinder head section so as to be able to inject fuel into the combustion chamber. The fuel injection valve 11 directly injects the fuel into the combustion chamber in accordance with a command of an ECU 20, which will be described below. An exhaust pipe 12 is connected to an end of an exhaust manifold, which is not shown, and the exhaust manifold is connected to an exhaust port that communicates with the combustion chamber, which is not shown. The exhaust port, the exhaust manifold, and the exhaust pipe 12 constitute an exhaust passage, through which exhaust gas discharged from the combustion chamber flows. A diesel oxidation catalyst (DOC) 13 and a diesel particulate filter (DPF) 14 are disposed in the exhaust pipe 12.

The DOC 13 is an exhaust gas control catalyst. More specifically, the DOC 13 has precious metals such as platinum and palladium as catalysts, and oxidizes unburned components (HC, CO) in the exhaust gas to purify the exhaust gas. That is, by the DOC 13, oxidation of HC leads to generation of water and $CO_2$, and oxidation of CO leads to generation of $CO_2$.

The DPF 14 is arranged on a downstream side of the DOC 13. The DPF 14 is a filter that catches particulates in the exhaust gas. More specifically, the DPF 14 includes plural passages, each of which is formed of a porous material (for example, a partition wall made of cordierite as one type of ceramic, for example). The DPF 14 collects the particulates that are contained in the exhaust gas passing through the partition wall in a pore surface of the partition wall.

The first detector includes the ECU 20. The ECU 28 is provided with a microcomputer, which includes a CPU, ROM, RAM, backup RAM, and an interface (IF), as a primary component. The CPU executes an instruction (a routine) stored in memory (the ROM) to realize a specified function.

The ECU 20 is connected to various actuators (the fuel injection valve 11 and the like) of the internal combustion engine 10. The ECU 20 sends a drive (command) signal to each of these actuators to control the internal combustion engine 10. Furthermore, the ECU 20 is connected to various types of sensors, which will be described below, and receives signals from these sensors.

An engine speed sensor (hereinafter referred to as an NE sensor) 21 measures a speed (an engine speed) NE of the internal combustion engine 10 and outputs a signal representing this engine speed NE.

A coolant temperature sensor 22 is disposed in a cylinder block section. The coolant temperature sensor 22 measures a temperature of a coolant (a coolant temperature THW) that cools the internal combustion engine 10, and outputs a signal representing this coolant temperature THW.

An accelerator pedal operation amount sensor 23 detects an operation amount of an accelerator pedal 23a (an accelerator operation amount) of the vehicle and outputs a signal representing an accelerator pedal operation amount AP.

A gas sensor 30 is a limiting current type gas sensor of one cell type and is disposed in the exhaust pipe 12 that constitutes the exhaust passage of the engine 10. The gas sensor 30 is disposed on a downstream side of the DOC 13 and the DPF 14 that are installed in the exhaust pipe 12.

Figure 2:
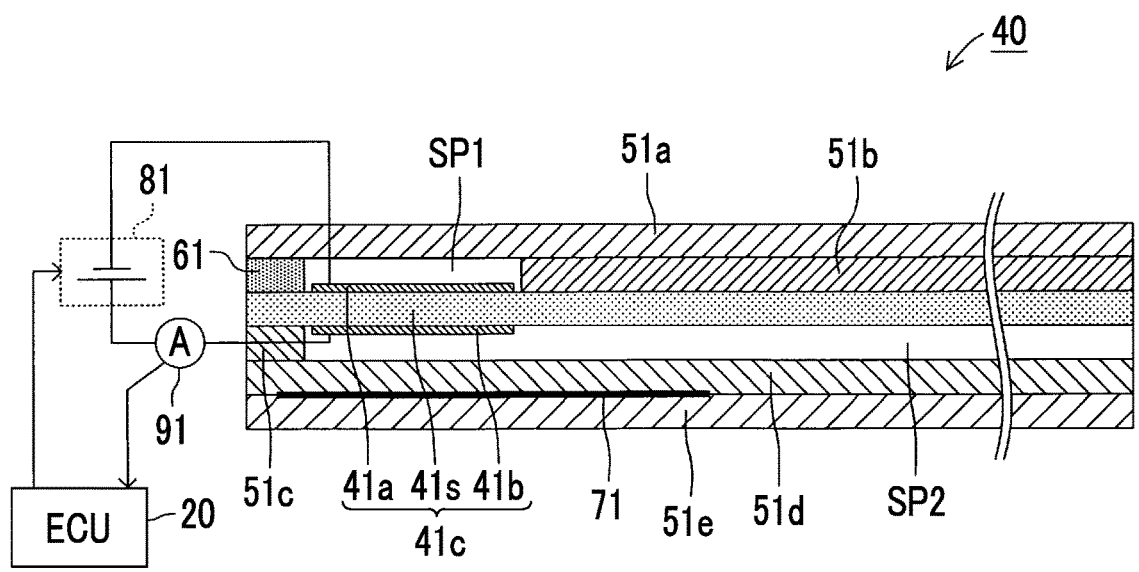
FIG. 2 is a schematic cross-sectional view of one configuration example of an element section of a gas sensor shown in FIG. 1.

Next, a description will be made on a configuration of the gas sensor 30 with reference to FIG. 2. An element section 40 provided in the gas sensor 30 includes a solid electrolyte body 41s, a first alumina layer 51a, a second alumina layer 51b, a third alumina layer 51c, a fourth alumina layer 51d, a fifth alumina layer 51e, a diffusion resistance body (a diffusion-controlled layer) 61, and a heater 71.

The solid electrolyte body 41s is a thin plate body that contains zirconia and the like and has oxide ion conductivity. Zirconia that forms the solid electrolyte body 41s may include elements such as scandium (Sc) and yttrium (Y).

The first to fifth alumina layers 51a to 51e are each a dense (gas-impermeable) layer (a dense thin plate body) that contains alumina.

The diffusion resistance body 61 is a porous diffusion-controlled layer and is a gas-permeable layer (thin plate body). The heater 71 is a thin cermet plate body that contains platinum (Pt) and ceramic (for example, alumina or the like), for example, and is a heat generation body that generates heat by energization. The heater 71 is connected to a power supply, which is not shown and is mounted on the vehicle, by lead wire, which is not shown. The heater 71 can change a heat generation amount when the ECU 20 controls an amount of power supplied from the power supply.

The layers of the element section 40 are stacked in an order of the fifth alumina layer 51e, the fourth alumina layer 51d, the third alumina layer 51c, the solid electrolyte body 41s, the diffusion resistance body 61 and the second alumina layer 51b, and the first alumina layer 51a from below.

An internal space SP1 is a space that is formed by the first alumina layer 51a, the solid electrolyte body 41s, the diffusion resistance body 61, and the second alumina layer 51b, and the exhaust gas of the internal combustion engine 10 as detected gas is introduced thereinto via the diffusion resistance body 61. That is, the internal space SP1 communicates with an interior of the exhaust pipe 12 of the internal combustion engine 10 via the diffusion resistance body 61. Accordingly, the exhaust gas in the exhaust pipe 12 is led as the detected gas into the internal space SP1. A first atmosphere intake passage SP2 is formed by the solid electrolyte body 41s, the third alumina layer 51c, and the fourth alumina layer 51d and is exposed to the atmosphere outside of the exhaust pipe 12.

A first electrode 41a is fixed to a surface on one side of the solid electrolyte body 41s (more specifically, a surface of the solid electrolyte body 41s that defines the internal space SP1). The first electrode 41a is a negative electrode. The first electrode 41a is a porous cermet electrode that contains platinum (Pt) as a primary component.

A second electrode 41b is fixed to a surface on the other side of the solid electrolyte body 41s (more specifically, a surface of the solid electrolyte body 41s that defines the first atmosphere intake passage SP2). The second electrode 41b is a positive electrode. The second electrode 41b is a porous cermet electrode that contains platinum (Pt) as a primary component.

The first electrode 41a and the second electrode 41b are arranged to oppose each other with the solid electrolyte body 41s being interposed therebetween. That is, the first electrode 41a, the second electrode 41b, and the solid electrolyte body 41s constitute an electrochemical cell 41c that has oxygen discharging capacity realized by an oxygen pumping effect. The electrochemical cell 41c is heated to an activation temperature by the heater 71.

Each layer of the solid electrolyte body 41s and the first to fifth alumina layers 51a to 51e is molded in a sheet shape by a doctor blade method, an extrusion method, or the like, for example. The first electrode 41a, the second electrode 41b, wires used to energize these electrodes, and the like are each formed by a screen printing method, for example. These sheets are stacked as described above and are calcined. In this way, the element section 40 with a structure as described above is integrally manufactured.

Note that the material constituting the first electrode 41a is not limited to the above material but can be selected from a material that contains a platinum group element such as platinum (Pt), rhodium (Rh), or palladium (Pd), an alloy thereof, or the like as a primary component. However, the material constituting the first electrode 41a is not particularly limited as long as SOx contained in the exhaust gas, which is led to the internal space SP1 via the diffusion resistance body 61, can be subjected to reductive decomposition when a voltage that is equal to or higher than a SOx decomposition initiation voltage (more specifically, a voltage of approximately 0.6 V or higher) is applied between the first electrode 41a and the second electrode 41b.

The gas sensor 30 further includes a power supply circuit 81 and an ammeter 91. The power supply circuit 81 and the ammeter 91 are connected to the above-described ECU 20.

The power supply circuit 81 can apply a specified voltage (hereinafter referred to as an applied voltage Vm) between the first electrode 41a and the second electrode 41b such that an electric potential of the second electrode 41b is higher than an electric potential of the first electrode 41a. The power supply circuit 81 can change the applied voltage Vm when being controlled by the ECU 20.

The ammeter 91 measures an output current Im as a current that flows between the first electrode 41a and the second electrode 41b (thus, a current flowing through the solid electrolyte body 41s), and outputs a measurement value to the ECU 20.

Next, a description will be made on an overview of actuation of the first detector. The first detector is configured to detect an oxygen concentration of the exhaust gas (the detected gas) that is discharged from the internal combustion engine 10. The first detector is configured to detect an air-fuel ratio (hereinafter referred to as an engine air-fuel ratio) A/F of air mixture in the combustion chamber of the internal combustion engine 10 on the basis of the oxygen concentration in the exhaust gas. Furthermore, the first detector is configured to determine presence or absence of SOx in a specified concentration or higher that is contained in the exhaust gas. Because several seconds are required from initiation of detection of the presence or the absence of SOx in the specified concentration or higher to termination of the detection, the first detector is configured to determine the presence or the absence of SOx in the specified concentration or higher in a state where the engine air-fuel ratio A/F is stable. Note that, as the specified concentration, an arbitrary concentration that is higher than 0% and corresponds to a desired detection level is selected.

Figure 3A:
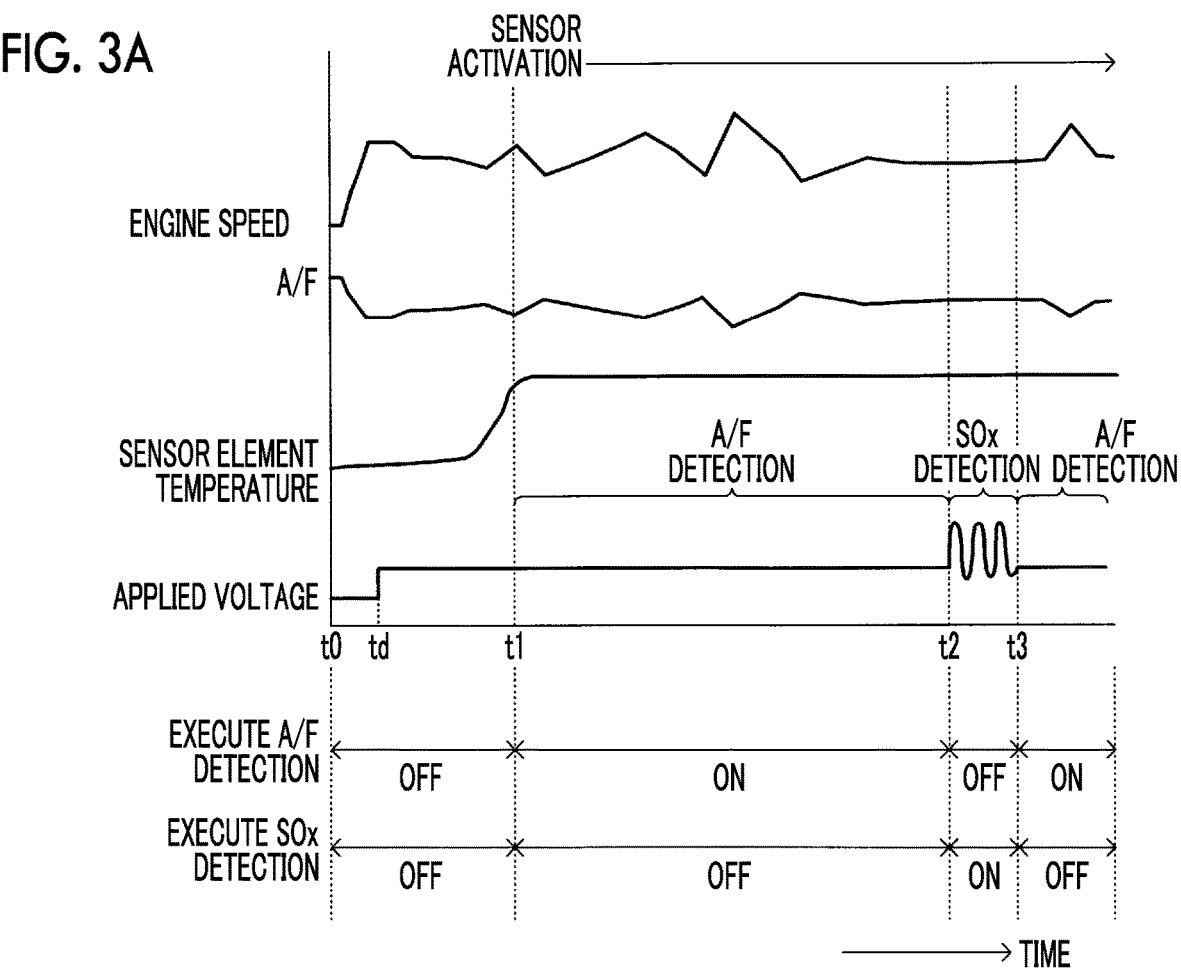
FIG. 3A is a time chart that illustrates an overview of actuation of the gas detector according to the first embodiment of the disclosure.

More specifically, as shown in FIG. 3A, at time t0 as a time point at which the internal combustion engine 10 is started, the first detector starts controlling the heater 71 such that the solid electrolyte body 41s is heated by the heater 71. In this way, a temperature of the solid electrolyte body 41s is increased to a specified temperature, at which the oxide ion conductivity appears, (hereinafter referred to as an activation temperature) or higher.

At time t1, the temperature of the solid electrolyte body 41s (a sensor element temperature) becomes equal to or higher than the activation temperature, and the gas sensor 30 is brought into a sensor active state. At this time, the first detector starts processing to detect the oxygen concentration in the exhaust gas and obtain the engine air-fuel ratio A/F on the basis of the oxygen concentration. Note that, at time td as a time point between the time t0 and the time t1, the first detector starts applying an oxygen concentration (A/F) detection voltage (more specifically, 0.3 V), which is appropriate for the detection of the oxygen concentration, between the first electrode 41a and the second electrode 41b. That is, the first detector sets the applied voltage Vm to the oxygen concentration detection voltage. In the cases where the temperature of the solid electrolyte body 41s is the activation temperature or higher and this applied voltage Vm is set as the oxygen concentration detection voltage, oxygen molecules are decomposed, and the oxygen pumping effect appears. However, the gas of the oxygen containing components (including SOx) is not decomposed except for oxygen.

The first detector successively detects the oxygen concentration from the time t1 and thereby monitors the engine air-fuel ratio A/F. Then, when a SOx detection initiation condition is satisfied (that is, when the engine air-fuel ratio A/F is brought into a stable state and the other conditions, which will be described below, are satisfied) at the time t2, the first detector starts the processing to detect the SOx concentration in the exhaust gas. Note that, in this specification, detection of the SOx concentration indicates both of detection (measurement) of the concentration of SOx itself that is contained in the exhaust gas and obtainment of a parameter that represents the concentration of SOx contained in the exhaust gas (the SOx concentration in the exhaust gas). As will be described below, this detector obtains the parameter that represents the SOx concentration in the exhaust gas (a parameter that is changed in accordance with the SOx concentration), and uses the parameter to determine whether SOx in the specified concentration or higher is contained in the exhaust gas.

That is, in a period from the time t1 to time immediately before the time t2, the first detector detects the engine air-fuel ratio A/F and stops detecting the engine air-fuel ratio A/F at the time t2 as a time point at which the first detector starts detecting the SOx concentration.

In a period from the time t2 to time immediately before time t3, the first detector executes applied voltage sweep within a specified applied voltage range. More specifically, after executing boosting sweep in which the applied voltage Vm is gradually boosted from a first voltage V1 to a second voltage V2, the first detector executes lowering sweep in which the applied voltage Vm is gradually lowered from the second voltage V2 to the first voltage V1. The first detector executes the applied voltage sweep that includes one time of the boosting sweep and one time of the lowering sweep as one cycle for plural cycles (n-th times). However, the first detector may only execute one cycle of the applied voltage sweep.

Figure 3B:
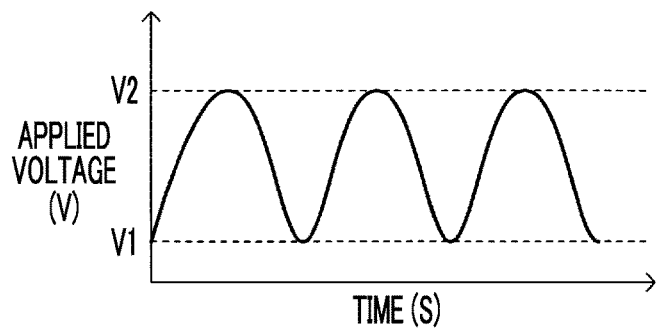
FIG. 3B is a graph that indicates a waveform of an applied voltage during detection of SOx.

More specifically, as shown in FIG. 3B, the first detector executes the applied voltage sweep by applying the voltage with a sine waveform between the first electrode 41a and the second electrode 41b. Note that the voltage waveform in this case is not limited to the sine wave shown m FIG. 3B and any of various waveforms can be adopted. For example, the voltage waveform in this case may be a non-sine wave as indicated in a graph of FIG. 3C (a waveform such as the voltage waveform during charging/discharging of a capacitor).

When terminating the detection of SOx concentration at the time t3, the first detector resumes the processing to detect the engine air-fuel ratio A/F. That is, the first detector sets the applied voltage Vm to the oxygen concentration detection voltage (0.3 V) at the time t3.

Next, a description will be made on the actuation of the first detector at the time when the first detector detects the above-described engine air-fuel ratio A/F. When the gas sensor 30 is brought into the sensor active state, in order to obtain the engine air-fuel ratio A/F, the first detector sets the applied voltage Vm to the oxygen concentration detection voltage (for example, 0.3 V) such that the first electrode 41a has the low electric potential and the second electrode 41b has the high electric potential. That is, the first electrode 41a functions as the negative electrode, and the second electrode 41b functions as the positive electrode. The oxygen concentration detection voltage is set to be equal to or higher than a voltage at which the decomposition of oxygen ($O_2$) is started in the first electrode 41a (a decomposition initiation voltage), is set to be a voltage at which a limiting current of oxygen, which will be described below, is observed, and is set to be a voltage that is lower than decomposition initiation voltages of the oxygen containing components other than oxygen. In this way, oxygen contained in the exhaust gas is subjected to the reductive decomposition in the first electrode 41a, which leads to generation of the oxide ions ($O^{2-}$).

These oxide ions are conducted to the second electrode 41b via the above solid electrolyte body 41s, become oxygen ($O_2$), and is discharged to the atmosphere through the first atmosphere intake passage SP2. As described above, movement of oxygen by the conduction of the oxide ions from the negative electrode (the first electrode 41a) to the positive electrode (the second electrode 41b) via the solid electrolyte body 41s is referred to as the oxygen pumping effect.

Due to the conduction of the oxide ions associated with this oxygen pumping effect, the current flows between the first electrode 41a and the second electrode 41b. The current that flows between the first electrode 41a and the second electrode 41b is referred to as the output current Im. In general, the output current Im has a tendency of being increased as the applied voltage Vm is boosted. However, a flow rate of the exhaust gas that reaches the first electrode 41a is limited by the diffusion resistance body 61 so that an oxygen consumption rate that is associated with the oxygen pumping effect eventually exceeds an oxygen supply rate to the first electrode 41a. That is, oxygen reductive decomposition reaction in the first electrode 41a (the negative electrode) is brought into a diffusion-controlled state.

Once oxygen reductive decomposition reaction in the first electrode 41a is brought into the diffusion-controlled state, the output current Im is not increased even when the applied voltage Vm is booted, and remains to be substantially constant. Such a characteristic is referred to as a limiting current characteristic. A range of the applied voltage where the limiting current characteristic appears (is observed) is referred to as a limiting current range. Furthermore, the output current Im within the limiting current range is referred to as the limiting current. A magnitude of the limiting current (a limiting current value) with respect to oxygen corresponds to the oxygen supply rate to the first electrode 41a (the negative electrode). As described above, because the flow rate of the exhaust gas that reaches the first electrode 41a is maintained to be constant by the diffusion resistance body 61, the oxygen supply rate to the first electrode 41a corresponds to the concentration of oxygen contained in the exhaust gas.

Accordingly, in the gas sensor 30, the output current (the limiting current) Im at the time when the applied voltage Vm is set to a specified voltage (more specifically, 0.3 V) within the limiting current range of oxygen corresponds to the concentration of oxygen contained in the exhaust gas. The first detector detects the concentration of oxygen contained in the exhaust gas as the detected gas by using the limiting current characteristic of oxygen as described above. Meanwhile, the engine air-fuel ratio A/F and the oxygen concentration in the exhaust gas establish a one-on-one relationship. Accordingly, the first detector stores this relationship in the ROM in advance and obtains the engine air-fuel ratio A/F on the basis of this relationship and the detected oxygen concentration. Note that the first detector may store a relationship between the limiting current of oxygen and the engine air-fuel ratio A/F in the ROM in advance and obtain the engine air-fuel ratio A/F on the basis of the relationship and the limiting current of oxygen.

Next, a description will be made on a method for detecting the SOx concentration in the exhaust gas (the detected gas). The above-described oxygen pumping effect also occurs to the oxygen containing components such as SOx (sulfur oxides) and $H_2O$ (water), each of which contains the oxygen atoms in the molecules. That is, when a voltage that is equal to or higher than the decomposition initiation voltage of each of these compounds is applied between the first electrode 41a and the second electrode 41b, each of these compounds is subjected to the reductive decomposition, which leads to the generation of the oxide ions. These oxide ions are conducted from the first electrode 41a to the second electrode 41b by the oxygen pumping effect. In this way, the output current Im flows between the first electrode 41a and the second electrode 41b.

However, the concentration of SOx that is contained in the exhaust gas is extremely low, and thus the current resulted from the decomposition of SOx is extremely small. Furthermore, a current resulted from the decomposition of each of the oxygen containing components other than SOx (for example, water, carbon dioxide, and the like) also flows between the first electrode 41a and the second electrode 41b. Thus, it is difficult to detect only the output current resulted from SOx with a high degree of accuracy.

In view of the above, as a result of the earnest investigation, the inventor of the present application has reached findings that the SOx concentration can accurately be detected by executing the applied voltage sweep that has the boosting sweep and the lowering sweep at a specified sweeping rate as one cycle at a time when the SOx concentration is detected.

The boosting sweep is processing to gradually boost the applied voltage Vm from the first voltage V1 to the second voltage V2. The lowering sweep is processing to gradually lower the applied voltage Vm from the second voltage V2 to the first voltage V1. Note that the first voltage V1 and the second voltage V2 each have the electric potential of the second electrode 41b with the electric potential of the first electrode 41a being a reference and each have a positive voltage value.

The first voltage V1 is set to a voltage within a voltage range (hereinafter referred to as a first voltage range) that is lower than the SOx decomposition initiation voltage (approximately 0.6 V) and that is higher than a minimum value of the applied voltage within a limiting current range of oxygen. Because the minimum value of the applied voltage within the limiting current range of oxygen depends on the engine air-fuel ratio A/F, a lower limit value of the first voltage range is also desirably changed in accordance with the engine air-fuel ratio A/F. More specifically, the lower limit value of the first voltage range is a voltage within a range from 0.2 to 0.45 V, for example, and an upper limit voltage of the first voltage range is 0.6 V, That is, the first voltage V1 is a voltage that is selected from a range of 0.2 V or higher and below 0.6 V.

The second voltage V2 is set to a voltage within a voltage range (hereinafter referred to as a second voltage range) that is higher than the SOx decomposition initiation voltage (approximately 0.6 V) and that is lower than an upper limit value (2.0 V) of the voltage, at which the solid electrolyte body 41s is not damaged. That is, the second voltage V2 is a voltage that is selected from a range of above 0.6 V and 2.0 V or lower.

Figure 4A:
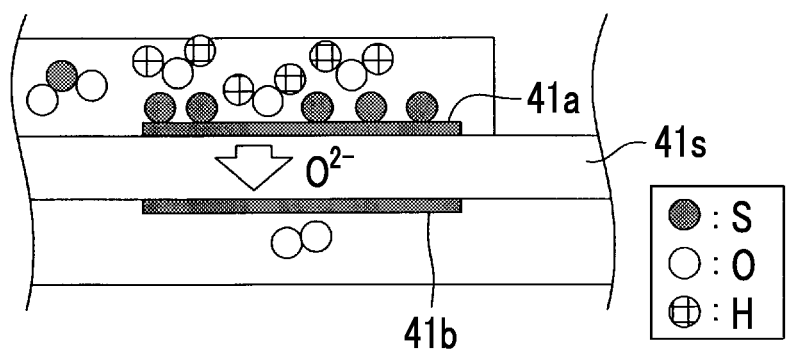
FIG. 4A is a schematic view that illustrates a SOx decomposition reaction occurred in an element section.

In a period in which the boosting sweep is executed, when the applied voltage Vm, which is applied between the first electrode 41a and the second electrode 41b, becomes equal to or higher than the SOx decomposition initiation voltage, as shown in FIG. 4A, the reductive decomposition of SOx contained in the exhaust gas leads to the generation of S and $O^{2-}$ in the first electrode 41a (the negative electrode).

As a result, a reductive decomposition product (S (sulfur)) of SOx is adsorbed to the first electrode 41a (the negative electrode).

Figure 4B:
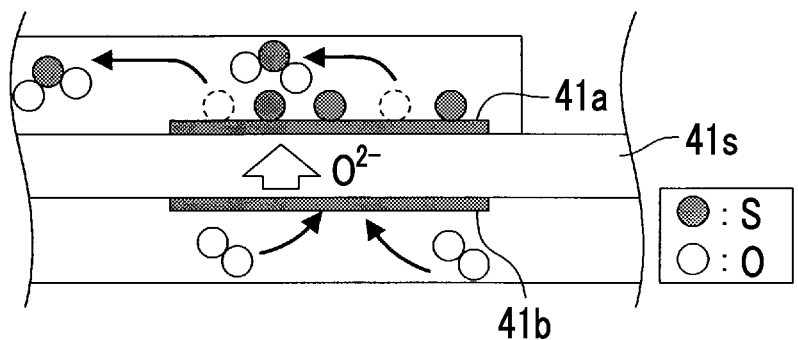
FIG. 4B is a schematic view that illustrates a sulfur reoxidation reaction occurred in the element section.

In a period in which the lowering sweep is executed, when the applied voltage Vm becomes lower than the SOx decomposition initiation voltage, as shown in FIG. 4B, S that is adsorbed to the first electrode 41a (the negative electrode) and $O^{2-}$ are reacted to produce SOx (hereinafter referred to as a S (sulfur) reoxidation reaction). At this time, the output current Im is changed as will be described below as a result of the S reoxidation reaction. Note that this change in the output current Im, which is associated with the S reoxidation reaction, is referred to as a reoxidation current change.

By the way, it has been found in the investigation by the inventor that the reoxidation current change, which yields a significant effect on the detection of the SOx concentration, does not always appear depending on the sweeping rate of the lowering sweep (a voltage lowering amount per specified elapsed time). A description will be made on this point with reference to FIG. 5A and FIG. 5B.

Figure 5A:
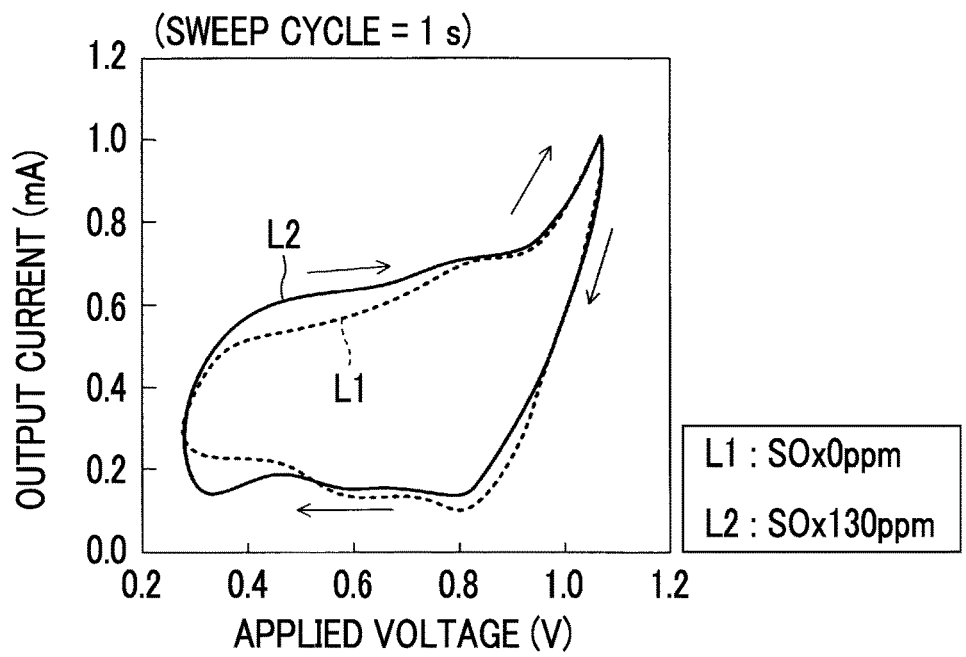
FIG. 5A is a graph that indicates a relationship between the applied voltage and an output current.
Figure 5B:
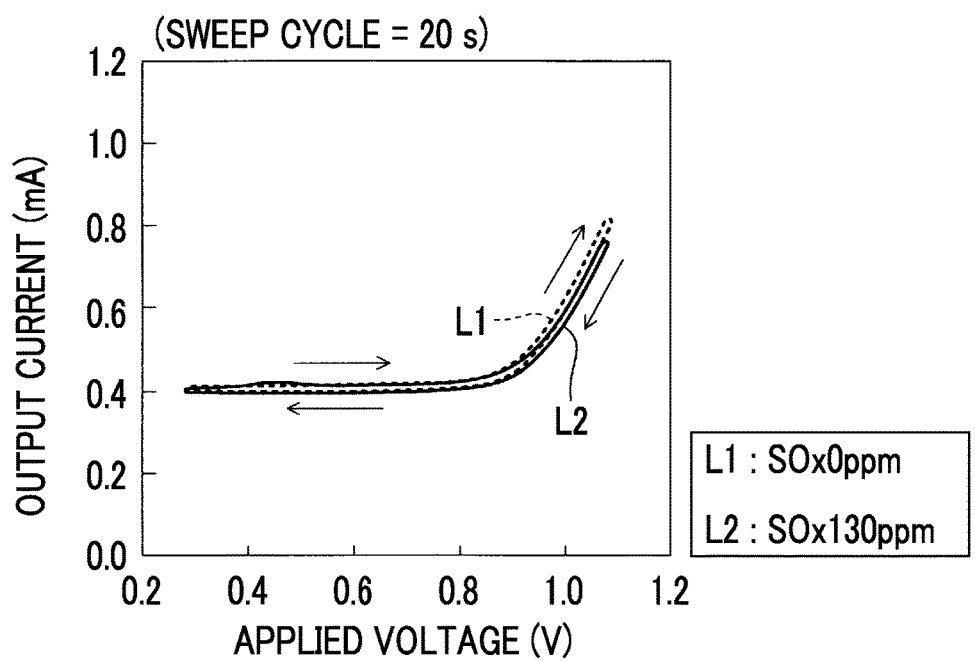
FIG. 5B is a graph that indicates a relationship between the applied voltage and the output current.

FIG. 5A is a schematic graph of a relationship between the applied voltage Vm and the output current Im at a time when a sweep cycle (that is, a sum of time required for the boosting sweep and time required for the lowering sweep, the cycle of the applied voltage sweep) is set to one second and the applied voltage sweep is executed. FIG. 5B is a schematic graph of a relationship between the applied voltage Vm and the output current Im at a time when the applied voltage sweep is executed at the slower sweeping rate (the sweep cycle of 20 seconds) than that in an example shown in FIG. 5A. Note that a waveform of the applied voltage Vm in this case is the sine waveform shown in FIG. 3B.

When both of the graphs are compared, a difference between the output current Im at a time when the SOx concentration of the detected gas is 0 ppm represented by a line L1 and the output current Im at a time when the SOx concentration of the detected gas is 130 ppm represented by a line L2 (a difference in the current value) in the voltage range below the SOx decomposition initiation voltage (0.6 V) appears more clearly in an example of FIG. 5A, in which the sweeping rate of the applied voltage sweep is higher, than an example of FIG. 5B. That is, a current change (the reoxidation current change) that yields the significant effect on the detection of the SOx concentration appears in the example of FIG. 5A. A mechanism of causing such a phenomenon is considered as follows.

That is, in the case where the sweeping rate is decreased to be lower than a specified rate, the S reoxidation reaction continuously and gradually progresses during the lowering sweep. Thus, the reoxidation current change, which yields the significant effect on the detection of the SOx concentration, does not appear. On the other hand, in the case where the sweeping rate is increased to be higher than the specified sweeping rate, the applied voltage is lowered while the S reoxidation reaction does not significantly progress during the lowering sweep. Then, once the applied voltage becomes a voltage within a certain voltage range at which the S reoxidation reaction is activated, it is considered that the S reoxidation reaction rapidly progresses. In this way, the current change that yields the significant effect on the detection of the SOx concentration appears.

Just as described, depending on the sweeping rate during the lowering sweep, a case where the current change that yields the significant effect on the detection of the SOx concentration appears and a case where the current change that yields the significant effect on the detection of the SOx concentration does not appear occur. Accordingly, when the lowering sweep is executed, it is required to set the sweeping rate to a specified rate at which the current change that represents the reoxidation current change and that yields the significant effect on the detection of the SOx concentration appears.

In the first detector, this specified rate is set to an appropriate rate, at which the current change that represents the reoxidation current change and that yields the significant effect on the detection of the SOx concentration change appears, by an experiment in advance.

According to the experiment, it has been found that this specified rate may be set to such a sweeping rate having a frequency F within a specified range (typically, a range of 0.1 Hz or higher and 5 Hz or below), for example, when the voltage in the sine waveform shown in FIG. 3B is applied between the first electrode 41a and the second electrode 41b. A lower limit value of the frequency F within this specified range is defined from such a perspective that a signal difference yielding the significant effect on the detection of the SOx concentration change (the reoxidation current change) can no longer be obtained when the frequency F is further lowered. Meanwhile, an upper limit value of the frequency F within this specified range is defined from such a perspective that the frequency F further contributes to causes of the current changes other than the SOx concentration (more specifically, capacity of the solid electrolyte body 41s and the like) when the frequency F is further increased.

Figure 3C:
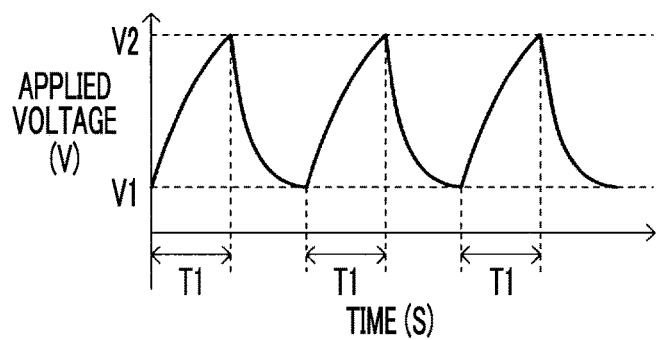
FIG. 3C is a graph that indicates another waveform of the applied voltage during the detection of SOx.

Meanwhile, according to the experiment, it has been found that this specified rate may be set to such a sweeping rate that a response time constant T1 of a voltage switching waveform falls within a specified range (typically, a range of 0.1 second or longer and 5 seconds or shorter) when the voltage in the non-sine waveform, which is associated with charging/discharging of the capacitor and is as shown in FIG. 3C, is applied between the first electrode 41a and the second electrode 41b. Note that the response time constant T1 corresponds to time required for the applied voltage to be changed from the lower limit voltage (a first voltage) to the upper limit voltage (a second voltage) within the specified range and vice versa.

Note that, when the specified ranges of the frequency F and the response time constant T1 described above are converted to the time required for the lowering sweep (that is, time required far the applied voltage reaches the first voltage V1 from the second voltage V2), each of the specified ranges is the range of 0.1 second or longer and 5 seconds or shorter. Thus, in some embodiments, the time falls within the range of 0.1 second or longer and 5 seconds or shorter.

Furthermore, as will be described below with reference to FIG. 6A and FIG. 6B, it has been found that the reoxidation current change significantly and primarily depends on a S concentration in the exhaust gas (the detected gas). In other words, there is g low possibility that the reoxidation current change is influenced by the gas (for example, water) that contains the oxygen containing components other than sulfur oxides (SOx) in the exhaust gas. That is, when the boosting sweep is executed, decomposed matters (for example, hydrogen as a decomposed matter of water, or the like) of the oxygen containing components other than sulfur oxides are not adsorbed to the first electrode 41a. Accordingly, in the period in which the lowering sweep is executed, such a phenomenon that such decomposed matters of the oxygen containing components other than sulfur oxides are subjected to the reoxidation reaction in the first electrode 41a and again become the oxygen containing components does not substantially occur. Thus, the SOx concentration in the exhaust gas can accurately be detected by using the reoxidation current change.

Figure 6A:
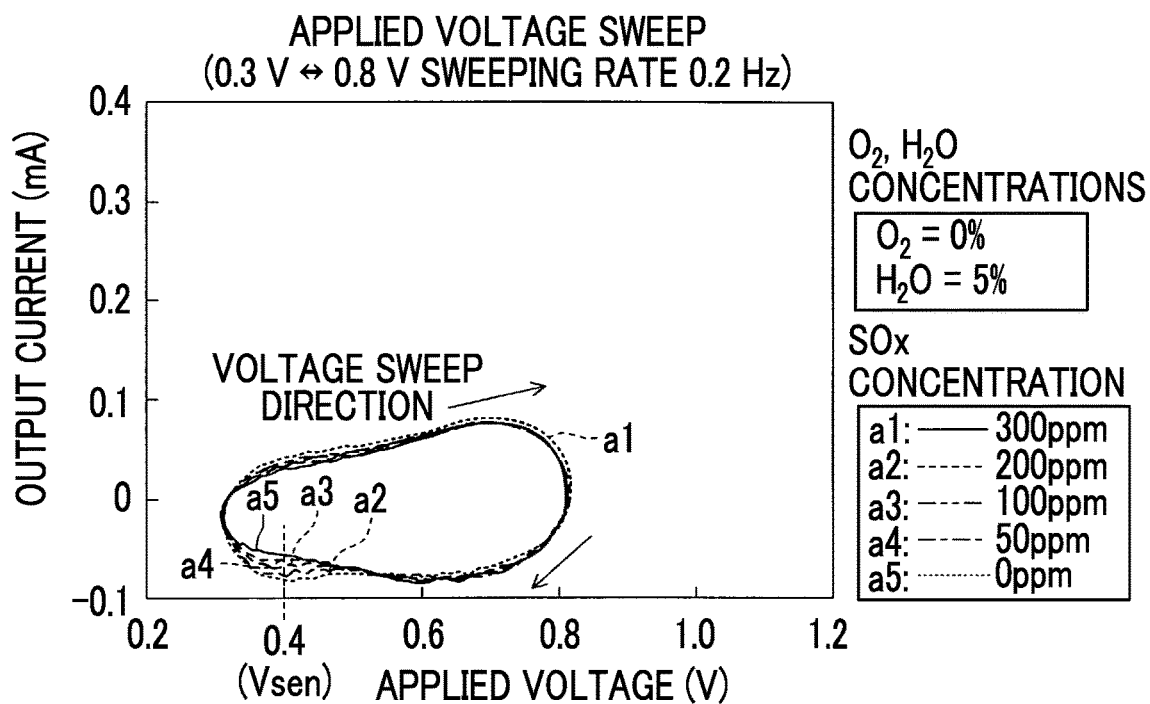
FIG. 6A is a graph that indicates a relationship between the applied voltage and the output current in the case where a SOx concentration of exhaust gas (detected gas) is changed to various concentrations.

FIG. 6A is a graph that schematically indicates a relationship between the applied voltage (the applied voltage in the sine waveform) Vm and the output current Im in the cases where the concentration of SOx contained in the exhaust gas (the detected gas) is changed to various values, the applied voltage range and the sweeping rate are set to be the same conditions, and then the applied voltage sweep is executed. According to an example shown in FIG. 6A, it can be confirmed that the output current Im (a reoxidation current Is) of a reoxidation current detection voltage Vsen (=0.4 V), which will be described below, becomes smaller as the concentration of SOx in the exhaust gas is increased.

Figure 6B:
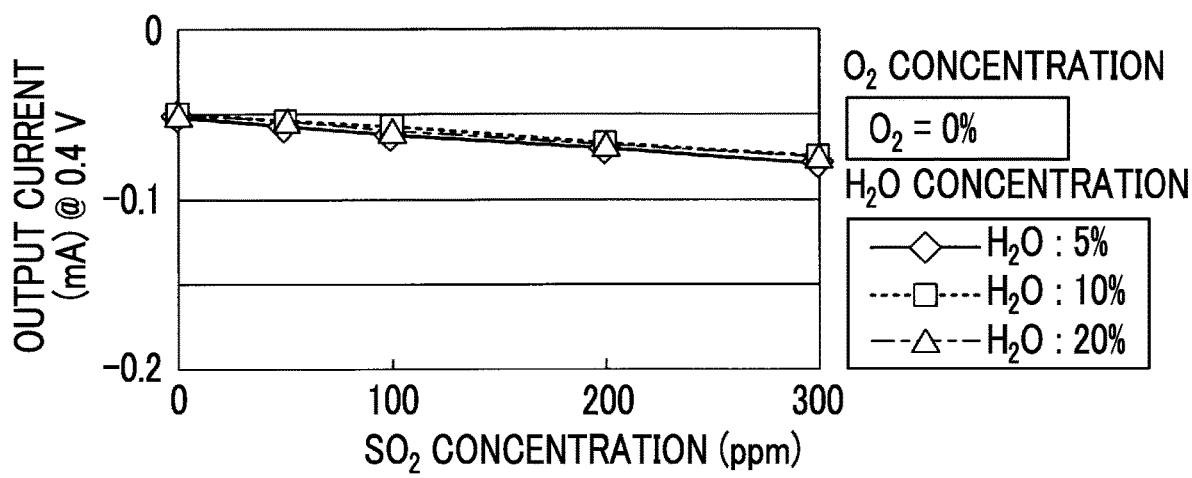
FIG. 6B is a graph that indicates a relationship between the output current and the SOx ($SO_2$) concentration in the case where an $H_2O$ concentration of the exhaust gas (the detected gas) is changed to various concentrations.

FIG. 6B is a graph of a relationship between the SOx concentration (an $SO_2$ concentration) and the output current Im (the reoxidation current Is) at the reoxidation current detection voltage Vsen in the cases where a concentration of $H_2O$ contained in the exhaust gas (the detected gas) is changed to various values and the applied voltage sweep is executed under the same conditions as those in FIG. 6A. According to an example shown in FIG. 6B, it can be confirmed that the output current Im (the reoxidation current Is) at the reoxidation current detection voltage Vsen (=0.4 V) depends on the SOx concentration in the exhaust gas but does not depend on the concentration of $H_2O$ in the exhaust gas. It is understood from what has been described so far that, when the reoxidation current change is used, the concentration of SOx in the exhaust gas can accurately be detected without being influenced by the oxygen containing components (for example, water) other than SOx in the exhaust gas. Accordingly, the first detector detects the SOx concentration (actually, the presence or the absence of SOx in the specified concentration or higher) by using this reoxidation current change.

The first detector obtains a parameter that appropriately (accurately) represents a degree of the reoxidation current change, and detects the SOx concentration on the basis of this parameter. More specifically, the first detector obtains the output current Im (hereinafter referred to as a reoxidation current Is) at a time when the applied voltage Vm falls within the first voltage range during the lowering sweep. The first voltage range corresponds to a range of the above-described reoxidation current detection voltage Vsen that is selected from the lower voltages than the SOx decomposition initiation voltage. Furthermore, the first detector obtains a base current Ibas, which will be described below. Then, the first detector obtains a difference Id (=Ibas−Is) between the base current Ibas and the reoxidation current Is as the parameter that (appropriately) represents the degree of the reoxidation current change.

The base current Ibas is the output current Im at the reoxidation current detection voltage Vsen during the lowering sweep at a time when the applied voltage sweep is executed under the same conditions (the same waveform, the same voltage range, and the same sweeping rate) as those in the case where the exhaust gas that does not contain S flows through the exhaust passage in advance and the SOx concentration in the exhaust gas is detected. The reoxidation current Is may be an average reoxidation current Iave that is obtained by averaging the plural output currents Im at the reoxidation current detection voltage Vsen that are obtained by executing the applied voltage sweep for plural times. Then, the first detector detects the SOx concentration on the basis of this parameter (the difference Id).

The first detector detects the SOx concentration as follows by using detection principle of the SOx concentration that has been described so far. The first detector executes the applied voltage sweep at the specified sweeping rate, at which the above-described reoxidation current change appears significantly. In this case, what is especially important is a lowering sweeping rate. At this time, the first detector determines the voltage range of the applied voltage sweep on the basis of the engine air-fuel ratio A/F that is detected by using the oxygen concentration in the exhaust gas. The first detector obtains the output current Im at the reoxidation current detection voltage Vsen during the lowering sweep as the reoxidation current Is. The first detector computes the difference Id (=Ibas−Is) between the base current Ibas and the reoxidation current Is. The first detector determines whether the SOx concentration is equal to or higher than the specified concentration on the basis of the difference Id. Note that, because the difference Id is a value that is equal to or larger than 0, the SOx concentration is equal to a magnitude of the difference Id.

More specifically, when detecting the SOx concentration, the first detector applies the voltage in the sine waveform shown in FIG. 3B between the first electrode 41a and the second electrode 41b. At this time, the first detector executes the applied voltage sweep (the boosting sweep and the lowering sweep) within the specified voltage range at such an above-described sweeping rate (the frequency within the above-described frequency range) that possibly leads to the current change that yields the significant effect on the detection of the SOx concentration described above.

Figure 7:
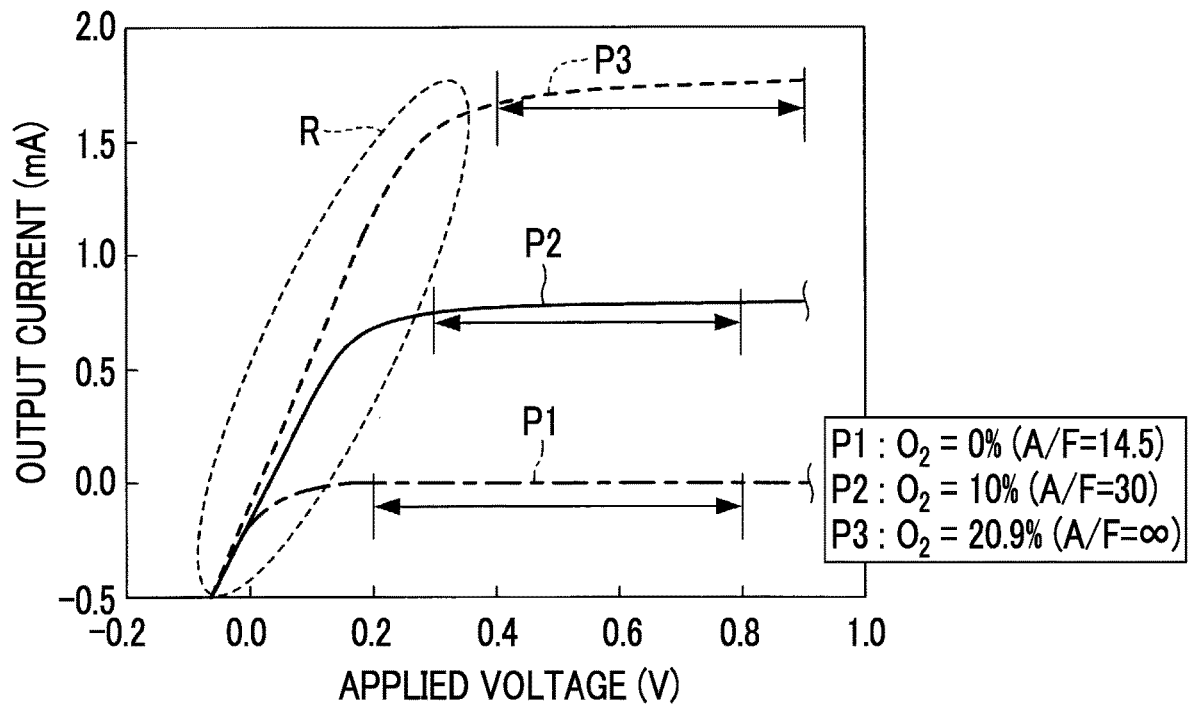
FIG. 7 is a graph that indicates a relationship between an air-fuel ratio A/F of air mixture in the combustion chamber and a limiting current range of oxygen.

That is, the first detector determines the voltage range of the applied voltage sweep (the upper limit voltage and the lower limit voltage of the applied voltage sweep) on the basis of the engine air-fuel ratio A/F. More specifically, as shown in FIG. 7, the lower limit voltage of the applied voltage sweep is defined to be a higher voltage than the minimum value of the voltage within the limiting current range of oxygen while preventing detection of the output current Im that falls within an internal resistance dependent region surrounded by a dotted line R. This internal resistance dependent region is a region in which the output current Im is increased along with boosting of the applied voltage Vm. The upper limit voltage of the applied voltage Vm within the internal resistance dependent region is gradually boosted as the engine air-fuel ratio A/F becomes leaner (the oxygen concentration in the exhaust gas is increased). Although the upper limit voltage of the applied voltage sweep may be constant, the upper limit voltage of the applied voltage sweep is defined to be boosted as the lower limit voltage of the applied voltage sweep is boosted. Note that the lower limit voltage within the voltage range of the applied voltage sweep will hereinafter be referred to as the lower limit voltage (the first voltage V1) of the applied voltage sweep.

More specifically, the tipper limit value of the applied voltage Vm within the internal resistance dependent region is increased as the engine air-fuel ratio A/F becomes leaner. Accordingly, the first detector boosts the lower limit voltage (the first voltage V1) of the applied voltage sweep as the engine air-fuel ratio A/F becomes leaner so that the voltage range of the applied voltage sweep does not enter this internal resistance dependent region R.

According to the experiment by the inventor, when A/F=14.5 (stoichiometric), the first voltage V1 may have a value that is selected from 0.2 V or higher, and the first detector sets the first voltage V1 at 0.2 V. When A/F=30, the first voltage V1 may have a value that is selected from 0.3 V or higher, and the first detector sets the first voltage V1 at 0.3 V. When A/F=an infinite value (an $O_2$ concentration=20.9%), the first voltage V1 may have a value that is selected from 0.4 V or higher, and the first detector sets the first voltage V1 at 0.4 V.

As it has already been described, in the cases where the boosting sweep and the lowering sweep are executed and SOx is contained in the exhaust gas, S (sulfur) that is produced by the decomposition of SOx during the boosting sweep is adsorbed to the first electrode 41a. Then, during the lowering sweep, S that has been adsorbed to the first electrode 41a, is oxidized again.

Figure 8:
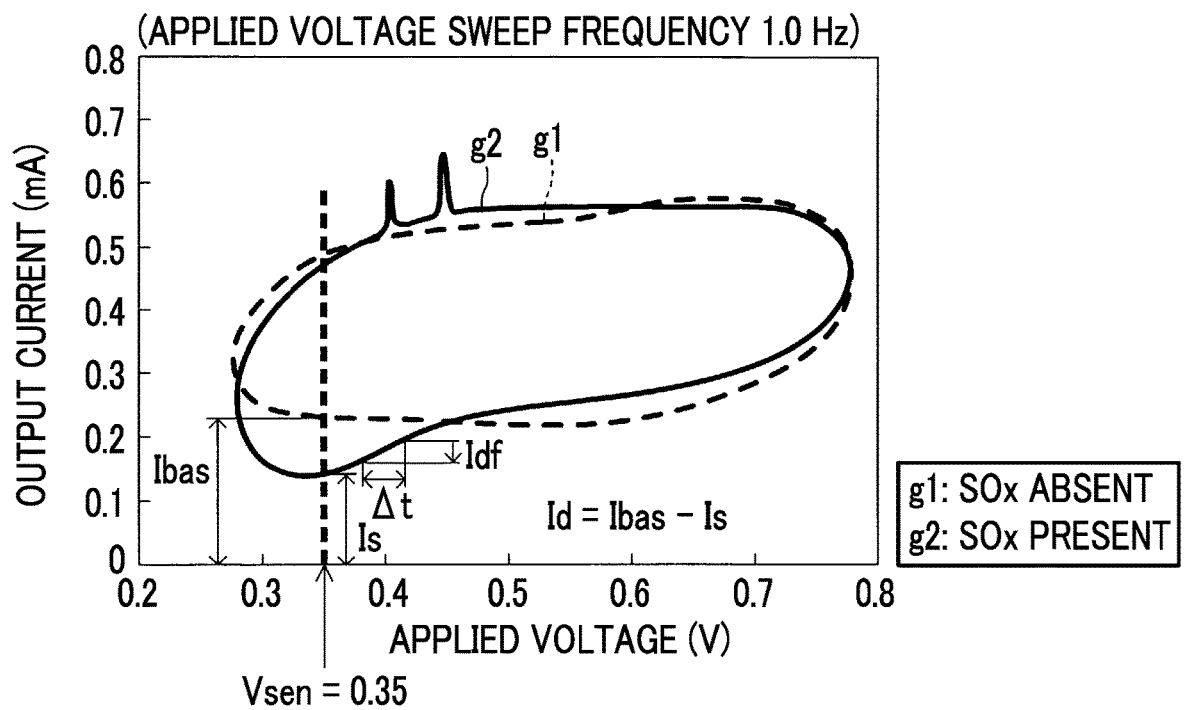
FIG. 8 is a graph that indicates a relationship between the applied voltage and the output current at a time when applied voltage sweep is executed.

The first detector detects the reoxidation current change by using the above-described parameter (=the difference Id) and thereby detects the SOx concentration. That is, the first detector obtains the output current Im (the base current Ibas) at a reoxidation detection voltage Vsen during the lowering sweep from the output current Im that is indicated by a line g1 in FIG. 8 and stores the output current Im in the ROM in advance. Furthermore, the first detector executes the applied voltage sweep and obtains the output current Im (the reoxidation current Is) at the reoxidation detection voltage Vsen during the lowering sweep from the output current Im that is indicated by a line g2 in FIG. 8, Moreover, the first detector compotes the difference Id (Id=Ibas−Is: the parameter representing the degree of the reoxidation current change) between the base current Ibas and the reoxidation current Is. The first detector detects the SOx concentration (determines the presence or the absence of SOx in the specified concentration or higher in the exhaust gas) on the basis of the difference Id (the magnitude of the difference Id).

Next, a description will be made on specific actuation of the first detector. Every time specified time elapses, the CPU of the ECU 20 (hereinafter simply referred to as the CPU) uses the gas sensor 30 to execute a sensor activation determination routine, an A/F detection routine, and a SOx detection routine that are respectively shown in flowcharts of FIG. 9 to FIG. 11.

Note that a value of an A/F detection request flag Xaf and a value of a SOx detection request flag Xs that are used in these routines are set to "0" in an initial routine executed by the CPU when an ignition key switch, which is not shown and is mounted on the vehicle, is switched from an OFF position to an ON position.

Figure 9:
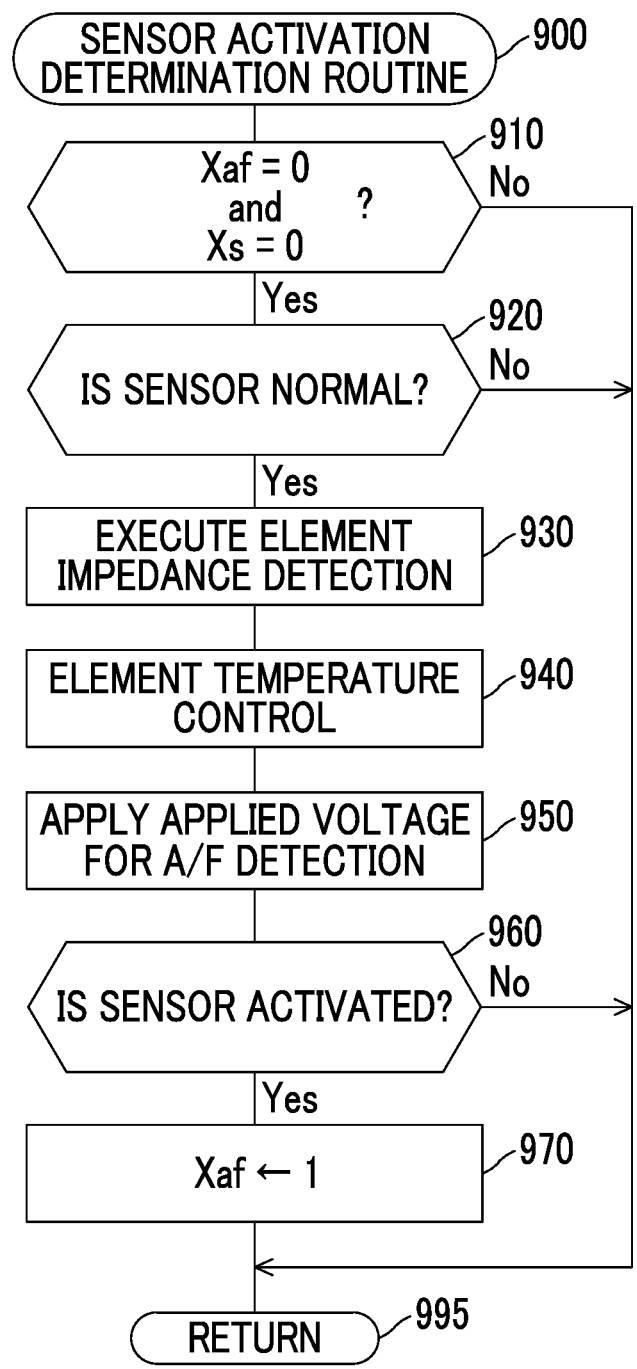
FIG. 9 is a flowchart of a sensor activation determination routine that is executed by a CPU of an ECU shown in FIG. 1.

At specified timing, the CPU starts processing from step 900 of the sensor activation determination routine shown in FIG. 9. Then, the processing proceeds to step 910, and the CPU determines whether both of the value of the A/F detection request flag Xaf and the value of the SOx detection request flag Xs are "0".

If a current time point is a time point immediately after the ignition key switch is switched to the ON position (immediately after the internal combustion engine 10 is started), both of the value of the A/F detection request flag Xaf and the value of the SOx detection request flag Xs are "0". In this case, the CPU determines "Yes" in step 910, and the processing proceeds to step 920. Then, the CPU determines whether the gas sensor 30 is normal by a well-known method. For example, the CPU determines that the gas sensor 30 is abnormal in the cases where the A/F is being detected during the last operation of the internal combustion engine 10, an operation state of the internal combustion engine 10 is changed from a fuel injection state to a fuel cut state, and the output current Im is not changed. Then, the CPU stores the determination in the backup RAM that can retain stored information even when the ignition key switch is OFF. Based on the stored information in the backup RAM, the CPU determines whether the gas sensor 30 is normal in step 920 of this routine.

If the gas sensor 30 is normal the CPU determines "Yes" in step 920, and the process proceeds to step 930. Then, the CPU detects element impedance (internal resistance of the solid electrolyte body 41s) for element temperature control on the basis of the output current Im at the time when the voltage (for example, a high-frequency voltage) is applied between the first electrode 41a and the second electrode 41b (for example, see Japanese Patent Application Publication No. 18-232220 (JP 10-232220 A) and Japanese Application publication No. 2002-71633 (JP 2002-71633 A)).

Thereafter, after the CPU sequentially executes the processing in step 940 and step 950, which will be described below, the processing proceeds to step 960. In step 940, the CPU executes heater energization control by target impedance feedback. That is, the CPU controls energization of the heater 71 such that the element impedance, which is obtained as temperature information in step 930, matches target impedance that is set in advance (for example, see JP 2002-71633 A and Japanese Patent Application Publication No. 2009-53108 (JP 2009-53108 A)). In step 950, the CPU applies the applied voltage (more specifically, 0.3 V) for the oxygen concentration detection (that is, for A/F detection) between the first electrode 41a and the second electrode 41b. That is, the CPU sets the applied voltage Vm to the applied voltage for the oxygen concentration detection.

When the processing proceeds to step 960, the CPU determines whether the gas sensor 30 is activated (whether the sensor is activated). More specifically, the CPU determines whether the temperature of the solid electrolyte body 41s, which is estimated on the basis of the element impedance obtained in step 930, is equal to or higher than an activation temperature threshold. If the gas sensor 30 is not activated, the CPU determines "No" in step 960. Then, the processing proceeds to step 995, and this routine is terminated once.

On the contrary, if the gas sensor 30 is activated, the CPU determines "Yes" in step 960. Then, the processing proceeds to step 970, and the CPU sets the value of the A/F detection request flag Xaf to "1". Thereafter, the processing proceeds to step 995, and the CPU terminates this routine once.

Note that if either one of the value of the A/F detection request flag Xaf and the value of the SOx detection request flag Xs is not "0" at the time point at which the CPU executes the processing in step 910, the CPU determines "No" in step 910. Then, the processing proceeds to step 995, and this routine is terminated once.

Next, a description will be made on the A/F detection routine with reference to FIG. 10. At specified timing, the CPU starts processing from step 1000 in FIG. 10. Then, the processing proceeds to step 1010, and the CPU determines whether the value of the A/F detection request flag Xaf is "1".

The A/F detection routine substantially functions in the case where the SOx detection request flag Xs is OFF (Xs=0) after the time point at which the gas sensor 30 is activated and the value of the A/F detection request flag Xaf is set to "1". Accordingly, if the value of the A/F detection request flag Xaf is not "1" (that is, the value of the A/F detection request flag Xaf is "0"), the CPU determines "No" in step 1010. Then, the processing proceeds to step 1095, and this routine is terminated once.

On the other hand, if the value of the A/F detection request flag Xaf is set to "1" by the processing in step 970 of FIG. 9, the CPU determines "Yes" in step 1010, and the processing proceeds to step 1020. Then, the CPU detects the oxygen concentration from the output current Im, which is obtained from the gas sensor 30, and applies the oxygen concentration to a specified lookup table (also referred to as a map) to compute the engine air-fuel ratio A/F. Thereafter, the processing proceeds to step 1030, and the CPU determines whether all conditions that constitute the following SOx detection condition are satisfied on the basis of information obtained from the various sensors (the NE sensor 21, the coolant temperature sensor 22, and the like).

The SOx detection condition is established when all of the following (1) to (3) conditions are satisfied. (1) The internal combustion engine 10 is in a state after being warmed (that is, the coolant temperature THW is equal to or higher than a warming coolant temperature THWth). (2) The gas sensor 30 is activated. The state is not a fuelcut state. (3) The engine air-fuel ratio A/F is stable. That is, the operation state of the internal combustion engine 10 is an idling state, or a driving state of the vehicle is a steady traveling state. Note that whether the operation state of the internal combustion engine 10 is the idling state is determined by determining whether states where the accelerator pedal operation amount AP is "0" and the engine speed NE is equal to or lower than a specified speed continue for specified idling time or longer. Whether the driving state of the vehicle is the steady traveling state is determined by determining whether a specified state continues for specified steady traveling threshold time or longer. The specified state is a state where a change amount of the accelerator pedal operation amount AP per unit time is equal to or smaller than a threshold operation change amount and a change amount of a vehicle speed, which is detected by an unillustrated vehicle speed sensor, per unit time is equal to or smaller than a threshold vehicle speed change amount. Note that, as the condition constituting the SOx detection condition, the following condition may be added. The SOx concentration is never detected after the ignition key switch is switched from the OFF position to the ON position and before the ignition key switch is switched to the OFF position again (that is, after the start of the internal combustion engine 10 this time).

If the SOx detection condition is established, the CPU determines "Yes" in step 1030 and sequentially executes processing in step 1040 to step 1070, which will be described below. Thereafter, the processing proceeds to step 1095, and this routine is terminated once.

In step 1040, the CPU obtains the A/F that is computed in step 1020. In step 1050, the CPU determines the voltage range of the applied voltage sweep (the lower limit voltage (the first voltage V1) and the upper limit voltage (the second voltage V2)) and the reoxidation current detection voltage Vsen by applying the obtained A/F to a lookup table M1. In step 1060, the CPU sets the value of the A/F detection request flag Xaf to "0" and sets the value of the SOx detection request flag Xs to "1". In step 1070, the CPU sets a value of a counter n that counts the number (cycle number) of the applied voltage sweep to "1".

On the other hand, if at least one of the conditions that constitute the SOx detection condition is not satisfied, the CPU determines "No" in step 1030. Then, the processing proceeds to step 1095, and this routine is terminated once.

Next, a description will be made on the SOx detection routine with reference to FIG. 11. At specified timing, the CPU starts processing from step 1100 in FIG. 11. Then, the processing proceeds to step 1105, and the CPU determines whether the value of the SOx detection request flag Xs is "1".

The SOx detection routine substantially functions in the case where the SOx detection condition is established (that is, in the case where the SOx detection request flag Xs is ON (Xs=1)). Accordingly, if the value of the SOx detection request flag Xs is not "1" (that is, the value of the SOx detection request flag Xs is "0"), the CPU determines "No" in step 1105. Then, the processing proceeds to step 1195, and this routine is terminated once.

Figure 10:
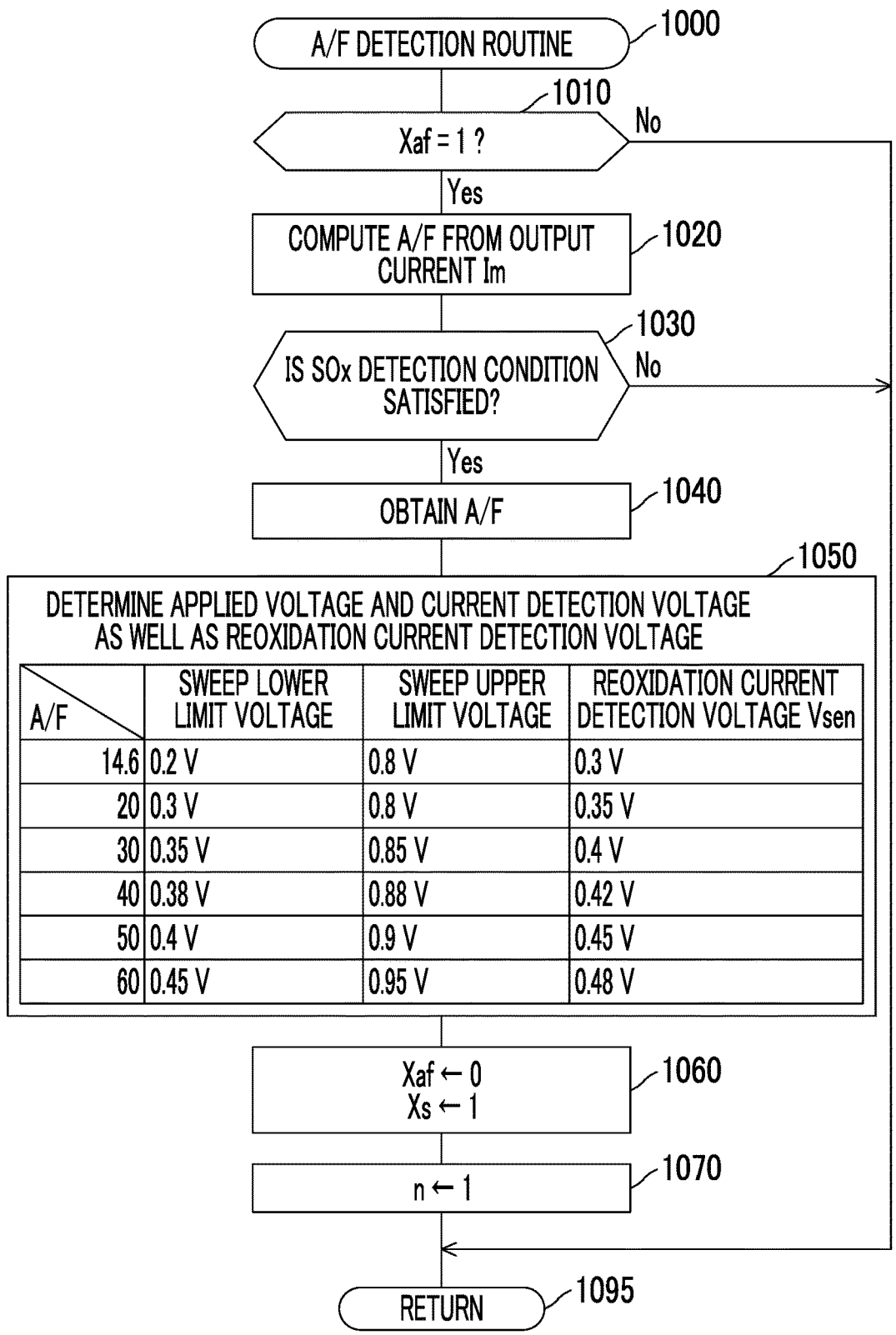
FIG. 10 is a flowchart of an A/F detection routine that is executed by the CPU of the ECU shown in FIG. 1.

On the other hand, if the value of the SOx detection request flag Xs is set to "1" by the processing in step 1060 of FIG. 10, the CPU determines "Yes" in step 1105, and the processing proceeds to step 1110. Then, the CPU executes the applied voltage sweep within the applied voltage range determined in step 1050 of FIG. 10. That is, the CPU starts processing to apply one cycle of the sine wave voltage (the frequency 1 Hz). Note that, if the applied voltage sweep is already being executed at a time point of the processing in step 1010, the CPU continues executing the applied voltage sweep. Next, the processing proceeds to step 1112, and the CPU determines whether a current time point is a time point during the lowering sweep and is a reoxidation current detection time point at which the applied voltage Vm matches the reoxidation current detection voltage Vsen. If the current time point is not the reoxidation current detection time point, the CPU determines "No" in step 1112. Then, the processing proceeds to step 1195, and this routine is terminated once. On the other hand, if the current time point is the reoxidation current detection time point, the CPU determines "Yes" in step 1112. Then, the processing proceeds to step 1115, and the CPU obtains the output current Im as a reoxidation current Is(n).

Thereafter, the processing proceeds to step 1120, and the CPU determines whether the counter n is equal to or larger than threshold sweep number nth (nth is an integer of 2 or larger).

If the counter n is not equal to or larger than the threshold sweep number nth, the CPU determines "No" in step 1120. Then, the processing proceeds to step 1160, and the CPU increases the value of the counter n by "1". Thereafter, the processing proceeds to step 1195, and this routine is terminated once.

On the other hand, if the counter n is equal to or larger than, the threshold sweep number nth, the CPU determines "Yes" in step 1120, sequentially executes processing in steps 1125 to 1140, which will be described below. Then, the processing proceeds to step 1145.

In step 1125, the CPU computes an average value (the average reoxidation current Iave) of the obtained reoxidation currents Is(1) to Is(nth). In step 1130, the CPU terminates the applied voltage sweep and changes the applied voltage Vm to the applied voltage for the A/F detection (more specifically, 0.3 V). In step 1135, the CPU obtains the base current Ibas and the threshold difference Idth by applying the voltage range of the applied voltage sweep of this time to a lookup table MapBse, which is not shown. In the voltage range, the lower limit voltage is the first voltage V1, and the upper limit voltage is the second voltage V2. At this time, the CPU may apply the engine air-fuel ratio A/F, which is obtained in step 1040 described above, to the lookup table MapBse. Note that, as described above, the base current Ibas is the output current Im at the reoxidation current detection voltage Vsen at the time when the applied voltage sweep is executed for the exhaust gas as the detected gas that does not contain SOx at the A/F and within the voltage range. The threshold difference Idth is an appropriate value used to determine whether SOx in the specified concentration or higher is contained in the exhaust gas, and is identified by executing the experiment or the like in advance. That is, sulfur (S) in an upper limit concentration within a permissible range is mixed in the fuel, and the difference Id at the time when the applied voltage sweep is executed under the same condition as above (the same condition as that in the case where the SOx concentration in the exhaust gas is actually detected) is set as the threshold difference Idth. Note that the same condition in this case is that the voltage waveform of the applied voltage sweep, the applied voltage range of the applied voltage sweep, the sweeping rate and the engine air-fuel ratio of the applied voltage sweep, and the like are the same. In step 1140, the CPU computes the difference Id=Ibas−Iave. Because the difference Id is a value that is equal to 0 or larger, the difference Id is equal to the magnitude of the difference Id.

When the processing proceeds to step 1145, the CPU determines whether the computed difference Id (thus, the magnitude of the difference Id) is equal to or larger than the threshold difference Idth. If the difference Id is equal to or larger than the threshold difference Idth, the CPU determines "Yes" in step 1145. Then, the processing proceeds to step 1150, and the CPU determines that SOx in the specified concentration (the upper limit concentration at the time when the threshold difference Idth is determined) or higher is contained in the exhaust gas. At this time, the CPU may store that SOx in the specified concentration or higher is contained in the exhaust gas (or S exceeding a permissible value is mixed in the fuel) in the backup RAM and may light a specified warning lamp. Thereafter, the processing proceeds to step 1155, and the CPU sets the value of the SOx detection request flag Xs to "0" and sets the value of the A/F detection request flag Xaf to "1". Thereafter, the processing proceeds to step 1195, and this routine is terminated once.

On the other hand, if the difference Id is not equal to or higher than the threshold difference Idth, the CPU determines "No" in step 1145. Then, the processing proceeds to step 1165, and the CPU determines that SOx in the specified concentration or higher is not contained in the exhaust gas. At this time, the CPU may store that SOx in the specified concentration or higher is not contained in the exhaust gas (or S exceeding the permissible value is not mixed in the fuel) in the backup RAM and may turn off the specified warning lamp. Thereafter, the processing proceeds to step 1155, and the CPU sets the value of the SOx detection request flag Xs to "0" and sets the value of the A/F detection request flag Xaf to "1". Thereafter, the processing proceeds to step 1195, and this routine is terminated once.

As it has been described so far, the ECU 20 of the first detector computes the difference Id between the reoxidation current Is and the base current Ibas as the parameter representing the degree of the reoxidation current change that is less likely to be influenced by the oxygen containing components other than SOx contained in the exhaust gas. Then, the ECU 20 is configured to determine whether SOx in the specified concentration or higher is contained in the exhaust gas on the basis of the computed difference Id. At the time, the ECU 20 obtains the reoxidation current Is after appropriately setting of the sweeping rate of the lowering sweep, the voltage range of the applied voltage sweep, and the like such that the large degree of the reoxidation current change appears.

More specifically, if the difference Id (the magnitude of the difference Id) is equal to or higher than the threshold difference Idth, the ECU 20 determines that SOx in the specified concentration or higher is contained in the exhaust gas. In addition, the ECU 20 is configured to determine that SOx in the specified concentration or higher is not contained in the exhaust gas if the difference Id (the magnitude of the difference Id) is lower than the threshold difference Idth. Accordingly, the CPU can accurately determine presence or absence of SOx in the specified concentration or higher contained in the exhaust gas.

Next, a description will be made on a gas detector according to a first modified example of the disclosure (hereinafter referred to as a first modified detector). The first modified detector differs from the first detector only in the following point. The first detector determines the presence or the absence of SOx in the specified concentration or higher in the exhaust gas by comparing the magnitude of the difference Id and the threshold difference Idth. Meanwhile, the first modified detector obtains the SOx concentration in the exhaust gas on the basis of the difference Id.

Figure 11:
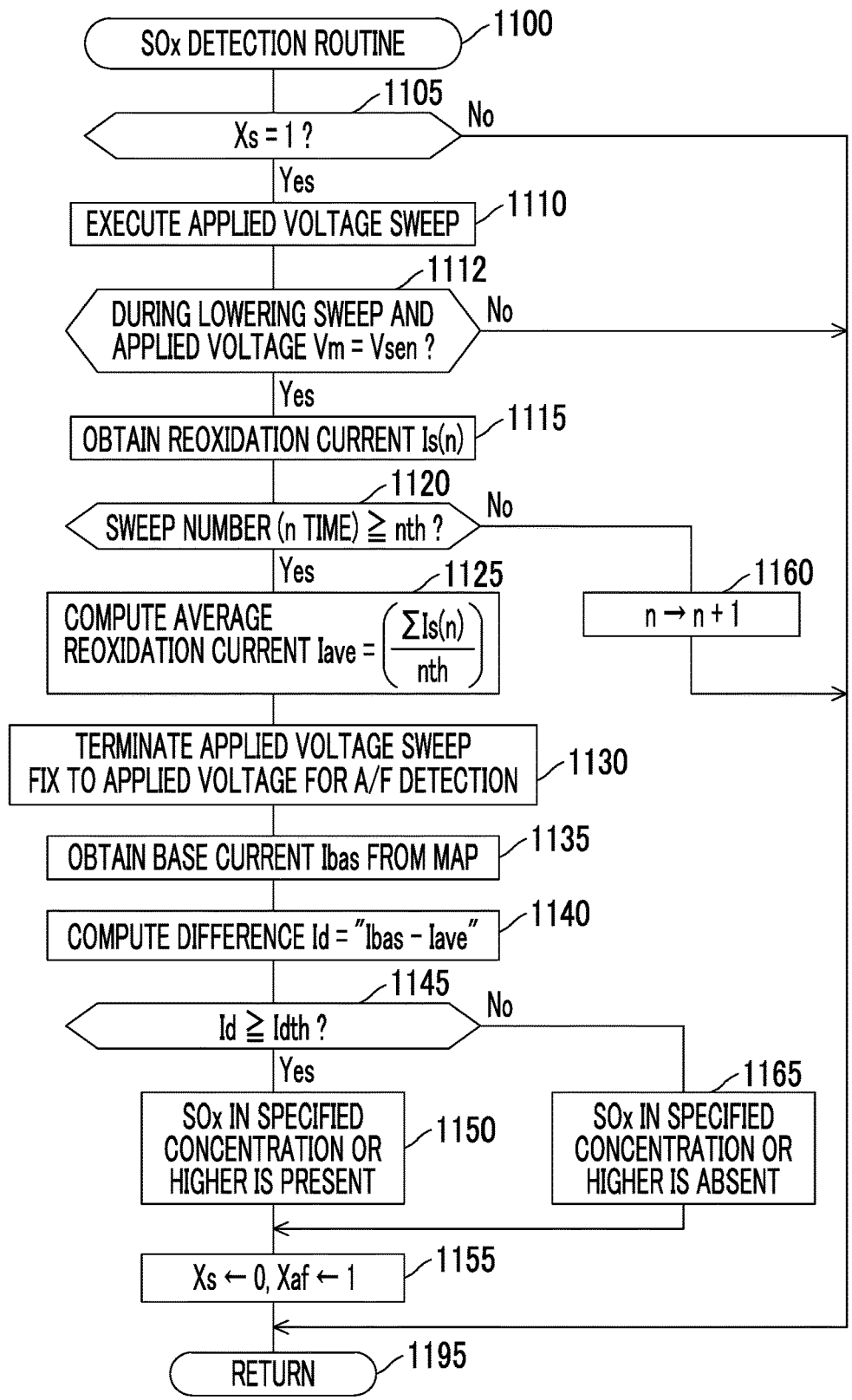
FIG. 11 is a flowchart of a SOx detection routine that is executed by the CPU of the ECU shown in FIG. 1.

More specifically, instead of step 1145, step 1150, and step 1165 of FIG. 11 described above, the CPU of the first modified detector executes the following processing in step 1170 (not shown). In step 1170, the CPU obtains the SOx concentration in the exhaust gas by applying the difference Id (the magnitude of the difference Id) to a lookup table MapND. Note that the ROM of the ECU 20 stores a relationship between the difference Id (the magnitude of the difference Id) and the concentration of sulfur oxides in the exhaust gas as the lookup table MapND. This lookup table MapND can be obtained by executing an experiment or the like in advance.

As described above, the ECU 20 of the first modified detector is configured to use the difference Id as the parameter representing the degree of the reoxidation current change that is less likely to be influenced by the oxygen containing components ether than SOx contained in the exhaust gas and to obtain the concentration of SOx in the exhaust gas that corresponds to the above difference Id by using the lookup table MapND stored in the ROM. Therefore, the concentration of sulfur oxides in the exhaust gas can accurately be detected.

Next, a description will be made on a gas detector according to a second embodiment of the disclosure (hereinafter referred to as a second detector). The second detector differs from the first detector in a point that a minimum value of a change amount Idf of the output current Im per specified elapsed time during the lowering sweep is used as the parameter representing the degree of the reoxidation current change.

Figure 12:
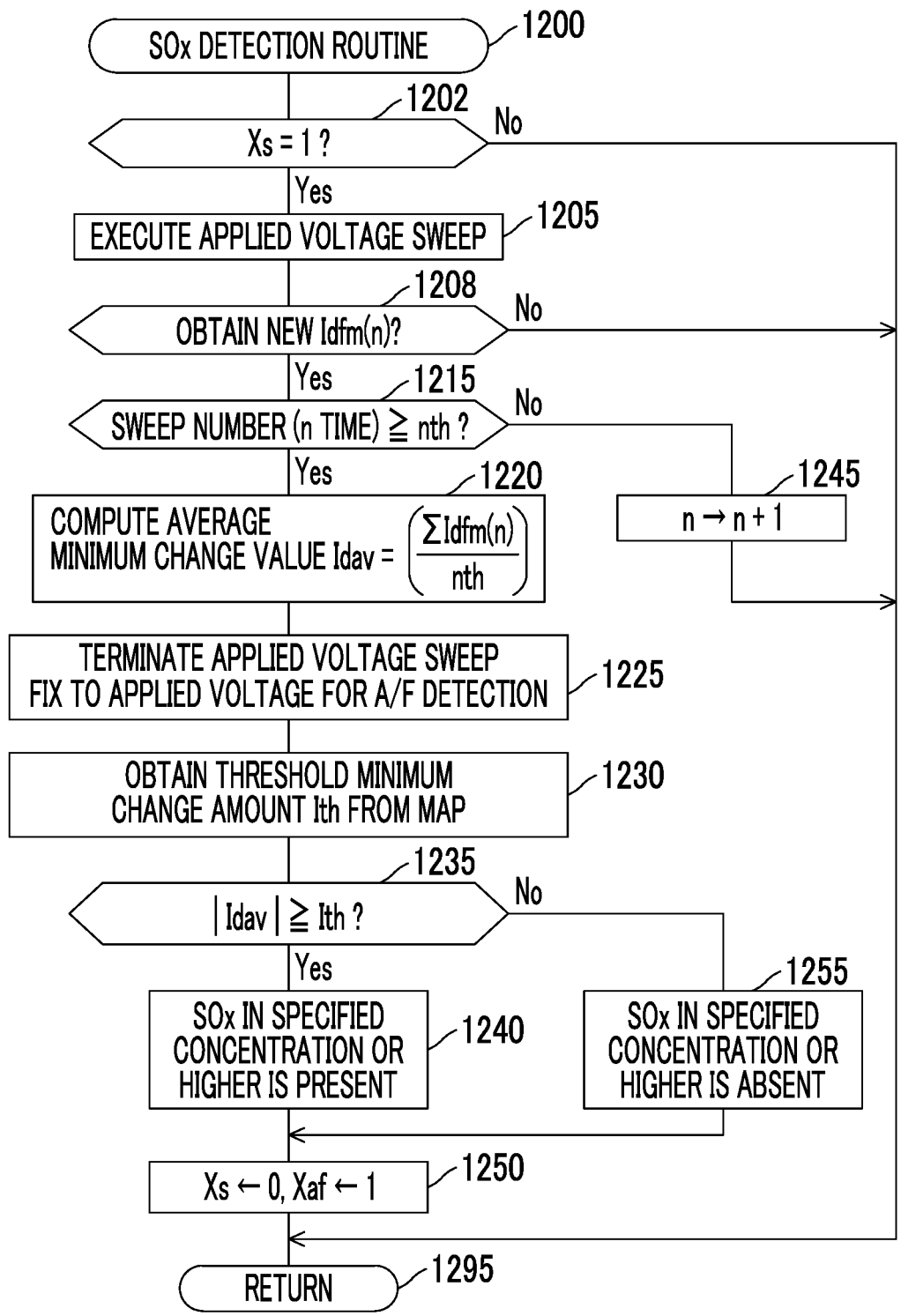
FIG. 12 is a flowchart of SOx detection routine that is executed by the CPU of the ECU provided in a gas detector according to a second embodiment of the disclosure.
Figure 13:
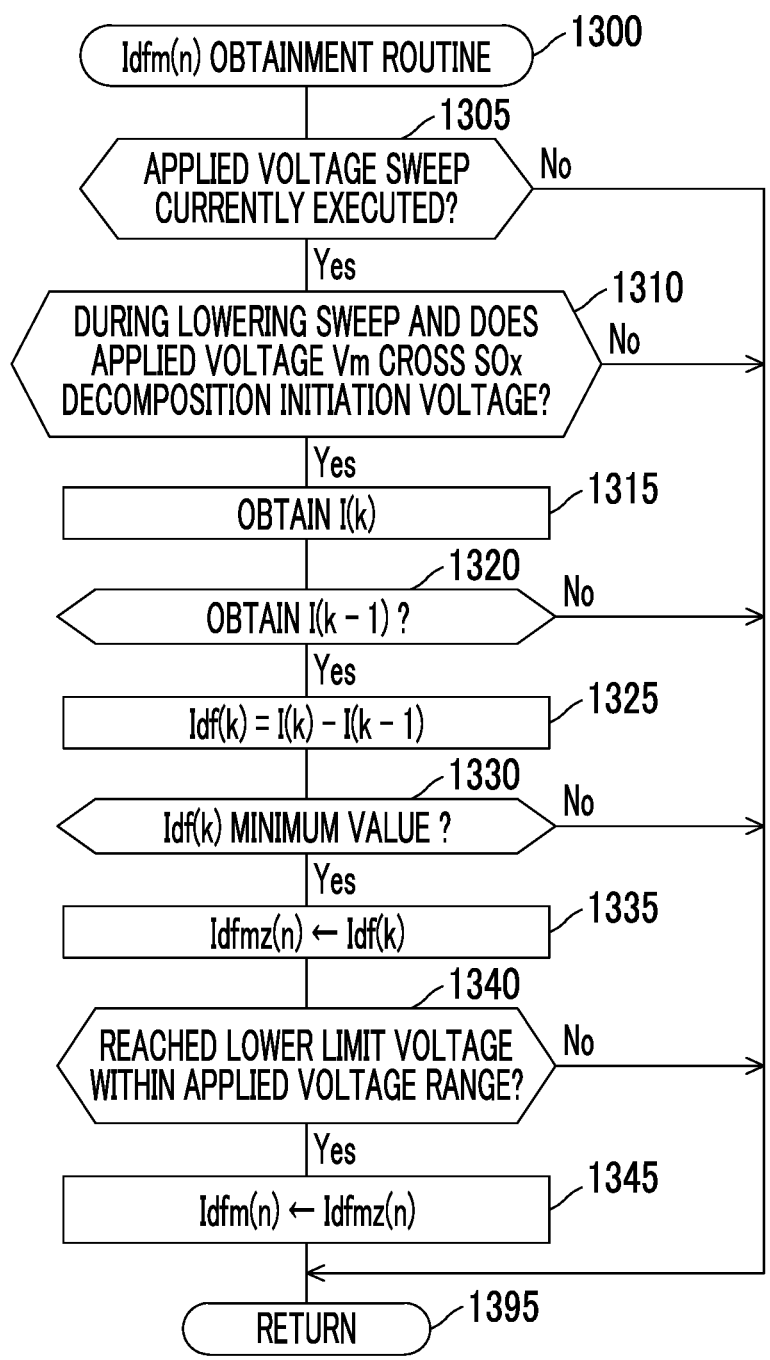
FIG. 13 is a flowchart an Idfm(n) obtainment routine that is executed by the CPU of the ECU provided in the gas detector according to the second embodiment of the disclosure.

More specifically, the second detector executes: the same sensor activation determination routine as the routine shown in FIG. 9; the A/F detection routine that differs from the routine shown in FIG. 10 only in a point that the following step is executed instead of step 1050; the SOx detection routine shown in FIG. 12 that replaces the routine shown in FIG. 11; and a minimum change amount Idfm(n) obtainment routine shown in FIG. 13.

Similar to the first detector, the second detector executes the applied voltage sweep, obtains the parameter representing the degree of the reoxidation current change during the lowering sweep in the applied voltage sweep, and uses the parameter to determine whether SOx in the specified concentration or higher is contained in the exhaust gas. Here, the second detector differs from the first detector in a point that the parameter thereof is the minimum change amount of the output current, which will be described below.

A specific method for detecting the reoxidation current change will be described. The second detector defines a specified voltage range of the voltage range, in which the reoxidation current change occurs, as a measurement voltage range. In this example, this measurement voltage range is set to the voltage range (that is, the above-described first voltage range) that is lower than the SOx decomposition initiation voltage (appropriately 0.6 V) and is higher than the minimum value of the applied voltage within the limiting current range of oxygen. In the case where the applied voltage Vm falls within the measurement voltage range thereof during the lowering sweep, the second detector detects the output current change amount (see the value Idf in FIG. 8) per specified elapsed time (unit time) Δt per elapsed time. The specified elapsed time Δt is 64 ms, for example. The output current change amount Idf is computed by subtracting the output current Im (k−1) at a time point before the current time point by the elapsed time Δt from the output current Im(k) at the current time point.

The second detector obtains the minimum value of the output current change amounts Idf, a plurality of which is obtained within the measurement voltage range as a minimum change amount Idfm. As the SOx concentration in the exhaust gas is increased, the reoxidation current change becomes significant, and the output current change amount Idf is reduced in conjunction with this (a negative value, and thus a magnitude (an absolute value) thereof obtains a large value). Thus, the minimum change amount Idfm is also reduced (a negative value, and thus a magnitude (an absolute value) thereof obtains a large value). Accordingly, the second detector obtains the minimum change amount Idfm as the parameter representing the degree of the reoxidation current change and detects the SOx concentration on the basis of the minimum change amount Idfm. Note that the second detector obtains an average minimum change amount Idav as the parameter representing the degree of the reoxidation current change, the average minimum change amount Idav being obtained by averaging measurement values of the minimum change amount Idfm that are obtained by executing the applied voltage sweep for plural times.

Next, a description will be made on specific actuation of the second detector. Every time specified time elapses, the CPU of the ECU 20 in the second detector executes a sensor activation determination routine that is the same as the routine of FIG. 9, an A/F detection routine (not shown) in which only step 1050 differs from that in the routine of FIG. 10, and a SOx detection routine in FIG. 12.

Because the sensor activation determination routine is the same as the sensor activation determination routine for the first detector that has already been described, the description thereon will not be made.

The A/F detection routine is the same as the A/F detection routine (the routine of FIG. 10) that is adopted by the first detector and that has already been described except for execution of the following step 1055 (not shown) instead of step 1050 in FIG. 10. In step 1055, the CPU determines the voltage range of the applied voltage sweep (the lower limit voltage (the first voltage V1) and the upper limit voltage (the second voltage V2)) by applying the engine air-fuel ratio A/F, which is obtained in step 1040, to a lookup table M2 (not shown). Note that the lookup table M2 is the same as the lookup table M1 (see step 1050 in FIG. 10) except that the item of the reoxidation current detection voltage is not provided.

A description will hereinafter the made on the SOx detection routine with reference to FIG. 12. At specified timing, the CPU starts processing from step 1200 in FIG. 12. Then, the processing proceeds to step 1202, and the CPU determines whether the value of the SOx detection request flag Xs is "1".

The SOx detection routine substantially functions in the case where the SOx detection condition described above is established (that is, in the case where the SOx detection request flag Xs is ON (Xs=1)). Accordingly, if the value of the SOx detection request flag Xs is not "1" (that is, the value of the SOx detection request flag Xs is "0"), the CPU determines "No" in step 1202. Then, the processing proceeds to step 1295, and this routine is terminated once.

On the other hand, if the value of the SOx detection request flag Xs is "1" (see step 1060), the CPU determines "Yes" in step 1202, and the processing proceeds to step 1205. Then, the CPU starts executing the applied voltage sweep within the applied voltage range determined in step 1055.

Meanwhile, the CPU executes the Idfm(n) obtainment routine, which is shown in the flowchart of FIG. 13, every time specified time $\Delta t$ (64 ms in this example) elapses, and thereby obtains the minimum change amount Idfm(n).

The minimum change amount Idfm(n) is a minimum value of the change amount Idf(k) of the output current Im per specified elapsed time $\Delta t$ (64 ms) in a period from a time point at which the applied voltage Vm becomes lower than the SOx decomposition initiation voltage (0.6 V or lower) to a time point at which the applied voltage Vm falls within the voltage range of the lower limit voltage (the first voltage V1) of the applied voltage sweep during the lowering sweep.

More specifically, the CPU starts processing from step 1300 in FIG. 13 at specified timing. Then, the processing proceeds to step 1305, and the CPU determines whether the applied voltage sweep is executed at the current time point (the applied voltage sweep is currently executed). If the applied voltage sweep is not currently executed, the CPU determines "No" in step 1305. Then, the processing proceeds to step 1395, and this routine is terminated once.

On the other hand, if the applied voltage sweep is currently executed, the CPU determines "Yes" in step 1305. Then, the processing proceeds to step 1310, and the CPU determines whether the current time point is a time point during the lowering sweep and whether the applied voltage Vm is changed from the voltage that is equal to or higher than the SOx decomposition initiation voltage to the voltage that is lower than the decomposition initiation voltage (that is, crosses the decomposition initiation voltage). If the determination condition in this step 1310 is not established, the CPU determines "No" in step 1310. Then, the processing proceeds to step 1395, and this routine is terminated once.

On the other hand, if the determination condition in this step 1310 is established, the CPU determines "Yes" in step 1310. Then, the processing proceeds to step 1315, and the CPU obtains the output current Im (=I(k)) at the current time point. Thereafter, the processing proceeds to step 1320, and the CPU determines whether the output current Im (=I(k−1)) in the last cycle of this routine is obtained.

If the current time point is a time point immediately after the determination condition in step 1310 is established, the CPU does not obtain the output current I(k−1) in the last cycle of this routine. Accordingly, in this case, the CPU determines "No" in step 1320. Then, the processing proceeds to step 1395, and this routine is terminated once.

On the other hand, if the current time point is not the time point immediately after it is determined that the determination condition in step 1310 is established, the CPU has already obtained the output current I(k−1). Accordingly, in this cases, the CPU determines "Yes" in step 1320. Then, the processing proceeds to step 1325, and the CPU computes the change amount Idf(k)=I(k)−I(k−1) of the output current Im per the specified elapsed time $\Delta t$. Note that the change amount Idf(k) per the specified elapsed time $\Delta t$ will hereinafter simply be referred to as the change amount Idf(k).

Thereafter, the processing proceeds to step 1330, and the CPU determines whether the change amount Idf(k) has the minimum value among the values of the change amount Idf(k) that have been obtained in this routine and the routine executed before this routine. That is, the CPU determines whether the change amount Idf(k) is smaller than a temporal minimum change amount Idfmz(n). Note that the temporal maximum change amount is set to "0" when the lowering sweep is started this time.

If the change amount Idf(k) has the minimum value, the CPU determines "Yes" in step 1330. Then, the processing proceeds to step 1335, and the CPU updates the temporal minimum change amount Idfmz(n) to the change amount Idf(k) obtained in this routine.

Thereafter, the processing proceeds to step 1340, and the CPU determines whether the applied voltage Vm has reached the lower limit voltage within the voltage range (the first voltage V1) of the applied voltage sweep (in other words, whether the current time point is a time point at which the lowering sweep of this time is terminated).

If the applied voltage Vm has not reached the lower limit voltage within the voltage range of the applied voltage sweep, the CPU determines "No" in step 1340. Then, the processing proceeds to step 1395, and this routine is terminated once.

On the other hand, if the applied voltage Vm has reached the lower limit voltage within the applied voltage range, the CPU determines "Yes" in step 1340. Then, the processing proceeds to step 1345, and the temporal minimum change amount Idfmz(n) during the applied voltage sweep in the current cycle is set as the minimum change amount Idfm(n). Then, the processing proceeds to step 1395, and this routine is terminated once.

By the way, after step 1205 in FIG. 12, the processing proceeds to step 1208, and the CPU determines whether the new minimum change amount Idfm(n) has been obtained. If the new minimum change amount Idfm(n) has not been obtained, the CPU determines "No" in step 1208. Then, the processing proceeds to step 1295, and this routine is terminated once.

On the other hand, if the new minimum change amount Idfm(n) has been obtained by the processing in step 1345 in FIG. 13, the CPU determines "Yes" in step 1208. Then, the processing proceeds to step 1215, and the CPU determines whether the value of the counter n, which indicates the number (the cycle number) of the applied voltage sweep, is equal to or larger than the threshold sweep number nth (nth is the integer of 2 or larger).

If the value of the counter n is not equal to or larger than the threshold sweep number nth, the CPU determines "No" in step 1215. Then, the processing proceeds to step 1245, and the CPU increases the value of the counter n by "1". Thereafter, the processing proceeds to step 1295, and this routine is terminated once.

On the other hand, if the counter n is equal to or larger than the threshold sweep number nth, the CPU determines "Yes" in step 1215, sequentially executes processing in step 1220, step 1225, and step 1230, which will be described below. Then, the processing proceeds to step 1235.

Step 1220: the CPU computes an average value of the obtained minimum change amounts Idfm(1) to Idfm(nth) (the average minimum change amount Idav). In step 1225, the CPU terminates the applied voltage sweep and changes the applied voltage Vm to the applied voltage for the A/F detection (more specifically, 0.3 V). In step 1230, the CPU obtains a threshold minimum change amount Ith by applying the A/F and the voltage range of the applied voltage sweep (the upper limit voltage and the lower limit voltage within the voltage range (the first voltage V1 and the second voltage V2)), which are determined in step 1055, which is not shown and is described above, to a lookup table (a map). The threshold minimum change amount Ith is an appropriate value used to determine whether SOx in the specified concentration or higher is contained in the exhaust gas, and is determined by an experiment or the like in advance.

When the processing proceeds to step 1235, the CPU determines whether an absolute value (|Idav|) of the average minimum change amount Idav, which is a magnitude of the computed average minimum change amount Idav, is equal to or larger than the threshold minimum change amount Ith. If the magnitude (|Idav|) of the average minimum change amount Idav is equal to or larger than the threshold minimum change amount Ith, the reoxidation current change is large. Thus, the CPU determines "Yes" in step 1235. Then, the processing proceeds to step 1240, and the CPU determines that SOx in the specified concentration or higher is contained in the exhaust gas. At this time, the CPU may store that SOx in the specified concentration or higher is contained in the exhaust gas in the backup RAM and may turn on the specified warning lamp. Thereafter, the processing proceeds to step 1250, and the CPU sets the value of the SOx detection request flag Xs to "0" and sets the value of the A/F detection request flag Xaf to "1". Then, the processing proceeds to step 1295, and this routine is terminated once.

On the other hand, if the magnitude of the computed the average minimum change amount Idav (the absolute value |Idav| of the average minimum change amount Idav) is not equal to or larger than the threshold minimum change amount Ith, the CPU determines "No" in step 1235. Then, the processing proceeds to step 1255, and the CPU determines that SOx in the specified concentration or higher is not contained in the exhaust gas. At this time, the CPU may store that SOx in the specified concentration or higher is not contained in the exhaust gas in the backup RAM and may turn off the specified warning lamp. Thereafter, the processing proceeds to step 1250, and the CPU sets the value of the SOx detection request flag Xs to "0" and sets the value of the A/F detection request flag Xaf to "1". Then, the processing proceeds to step 1295, and this routine is terminated once.

As it has been described so far, the ECU 20 of the second detector computes the minimum change amount Idfm, which is the minimum value of the change amount Idf of the output current Im per specified elapsed time Δt within the first voltage range during the lowering sweep, as the parameter representing the degree of the reoxidation current change that is less likely to be influenced by the oxygen containing components other than SOx contained in the exhaust gas. Then, the ECU 20 of the second detector is configured to detect the presence or the absence of SOx in the specified concentration or higher that is contained in the exhaust gas on the basis of the computed minimum change amount Idfm (actually, on the basis of the average minimum change amount Idav computed on the basis of the minimum change amount Idfm). At the time, the ECU 20 appropriately sets the sweeping rate of the lowering sweep, the voltage range of the applied voltage sweep, and the like such that the large degree of the reoxidation current change appears, and then obtains the minimum change amount Idfm.

More specifically, if the magnitude (|Idav|) of the average minimum change amount Idav is equal to or higher than the threshold minimum change amount Ith, the ECU 20 determines that SOx in the specified concentration or higher is contained in the exhaust gas. Then, the ECU 20 is configured to determine that SOx in the specified concentration or higher is not contained in the exhaust gas if the magnitude (|Idav|) of the average minimum change amount Idav is lower than the threshold minimum change amount Ith. Accordingly, the ECU 20 can accurately determine the presence or the absence of SOx in the specified concentration or higher contained in the exhaust gas.

Next, a description will be made on a gas detector according to a second modified example of the disclosure (hereinafter referred to as a "second modified detector"). The second modified detector differs from the second detector only in the following point. The second detector determines whether SOx in the specified concentration or higher is contained in the exhaust gas by comparing the magnitude (|Idav|) of the average minimum change amount Idav, which is computed on the basis of the minimum change amount Idfm, and the threshold difference Idth. On the other hand, the second modified detector obtains the SOx concentration in the exhaust gas on the basis of the minimum change amount Idfm (or the magnitude (|Idav|) of the average minimum change amount Idav computed on the basis of the minimum change amount Idfm).

More specifically, instead of step 1235, step 1240, and step 1255 in FIG. 12 described above, the CPU of the second modified detector executes the following processing in step 1270 (not shown). In step 1270, the CPU applies the average minimum change amount Idav, which is computed on the basis of the minimum change amount Idfm, to the lookup table MapNDdfm and thereby obtains the SOx concentration in the exhaust gas. Note that the ROM of the ECU 20 stores the concentration of sulfur oxides in the exhaust gas, which corresponds to the average value Idav of the minimum change amount Idfm, as the lookup table MapNDdfm. This lookup table MapNDdfm can be obtained by the experiment or the like in advance.

According to the second modified detector, the ECU 20 is configured to use the above minimum change amount Idfm (the average minimum change amount Idav computed on the basis of the minimum change amount Idfm) as the parameter representing the degree of the reoxidation current change that is less likely to be influenced by the oxygen containing components other than SOx contained in the exhaust gas and thereby obtain the concentration of SOx in the exhaust gas, which corresponds to the average minimum change amount Idav, from the lookup table MapNDdfm stored in the ROM. Therefore, the concentration of sulfur oxides in the exhaust gas can accurately be detected.

The specific description has been made so far on each of the embodiments and each of the modified examples of the disclosure. However, the disclosure is not limited to each of the embodiments and each of the modified examples described above, and various modified examples (other modified examples) that are based on the technical idea of the disclosure can be adopted.

For example, the above-described first detector may set the plural reoxidation current detection voltages Vsen and then determine the presence or the absence of SOx in the specified concentration or higher in the exhaust gas on the basis of an integral value that is obtained by integrating the plural differences Id obtained from each of the plural reoxidation current detection voltages Vsen.

Furthermore, for example, the above-described first detector obtains the engine air-fuel ratio A/F in step 1040 and step 1050 in FIG. 10. Then, the above-described first detector determines the lower limit voltage and the upper limit voltage within the voltage range of the applied voltage sweep as well as the reoxidation current detection voltage Vsen on the basis of the obtained A/F.

Meanwhile, in another modified example of the first and second detectors, the oxygen concentration, which is detected on the basis of the output current Im in the case where the applied voltage Vm is set as the applied voltage for the oxygen concentration detection, may be detected in a step substituting step 1020. Then, the lower limit voltage and the upper limit voltage within the voltage range of the applied voltage sweep as well as the reoxidation current detection voltage Vsen may be determined on the basis of the oxygen concentration. In this case, the lookup table M1 is a table that defines a relationship between the oxygen concentration and "the lower limit voltage and the upper limit voltage within the voltage range of the applied voltage sweep as well as the reoxidation current detection voltage Vsen".

Similarly, in yet another modified example of the first and second detectors, the lower limit voltage and the upper limit voltage within the voltage range of the applied voltage sweep as well as the reoxidation current detection voltage Vsen may be determined on the basis of the output current Im itself in the case where the applied voltage Vm is set as the applied voltage for the oxygen concentration detection. In this case, the lookup table M1 is a table that defines a relationship between the output current Im and "the lower limit voltage and the upper limit voltage within the voltage range of the applied voltage sweep as well as the reoxidation current detection voltage Vsen".

For example, in the above-described second detector, the presence or the absence of SOx in the specified concentration or higher in the exhaust gas may be determined by comparing the change amount $Idf(k)=I(k)-I(k-1)$ and the threshold. Furthermore, the presence or the absence of SOx in the specified concentration or higher in the exhaust gas may be determined on the basis of an integral value that is obtained by integrating the change amount $Idf(k)=I(k)-I(k-1)$.

Furthermore, the voltage waveform of the applied voltage sweep is not limited to the waveforms shown in FIG. 3B and FIG. 3C and may be an arbitrary waveform (for example, a triangular wave) as long as the lowering sweep is executed at a lowering rate such that the reoxidation current change caused by the continuous change in the voltage and the reoxidation reaction of sulfur adsorbed to the first electrode 41*a* becomes extremely significant from a certain time point during the lowering sweep.

What is claimed is:
1. A control device for a gas detector,
the gas detector including an element section, a power supply circuit, and a current detector,
the element section including an electrochemical cell and a diffusion resistance body, and being provided in an exhaust passage of an internal combustion engine,
the electrochemical cell including a solid electrolyte body that has oxide ion conductivity, a first electrode and a second electrode, the first electrode and the second electrode being respectively provided on surfaces of the solid electrolyte body,
the diffusion resistance body being constituted a porous material through which exhaust gas flowing through the exhaust passage is passable,
the element section being configured that the exhaust gas flowing through the exhaust passage reaches the first electrode through the diffusion resistance body,
the power supply circuit being configured to apply a voltage between the first electrode and the second electrode, and
the current detector being configured to detect an output current that is a current flowing between the first electrode and the second electrode,
the control device comprising:
an electronic control unit configured to control an applied voltage that is the voltage applied between the first electrode and the second electrode by using the power supply circuit;
the electronic control unit configured to obtain the output current by using the current detector;
the electronic control unit configured to execute lowering sweep after executing boosting sweep by using the power supply circuit when the electronic control unit determines that an air-fuel ratio of air mixture supplied to the internal combustion engine is in a stable state,
the boosting sweep being control to boost the applied voltage from a first voltage to a second voltage, the first voltage being selected from a first voltage range that is lower than a decomposition initiation voltage of sulfur oxides, and the second voltage being selected from a second voltage range that is higher than the decomposition initiation voltage of sulfur oxides,
the lowering sweep being control to lower the applied voltage from the second voltage to the first voltage at a specified lowering rate; and
the electronic control unit configured to obtain a specified parameter based on the output current and execute one of a specified determination and a specified detection based on the specified parameter,
the specified determination being a determination on whether sulfur oxides in a specified concentration or higher are contained in the exhaust gas,
the specified detection, being detection of a concentration of the sulfur oxides in the exhaust gas,
the specified parameter being a specified change and correlated with a change occurred to the output current, the output current being increased as the concentration of the sulfur oxides contained in the exhaust gas is increased,
the specified change being a change occurred to the output current due to the current that flows between the first electrode and the second electrode at a time when a reoxidation reaction of specified sulfur in the first electrode leads to generation of sulfur oxides, the specified sulfur being sulfur that is adsorbed to the first electrode at a time when the applied voltage becomes lower than the decomposition initiation voltage of sulfur oxides during the lowering sweep, the specified lowering rate being set to such a rate that a rate of the reoxidation reaction of the specified sulfur is rapidly increased at a time point at which the applied voltage becomes a voltage that falls within the first voltage range and also falls within a higher voltage range than the first voltage.

2. The control device for the gas detector according to claim 1, wherein the electronic control unit is configured to store a second output current at a time point that an applied voltage becomes the reoxidation current detection voltage during the lowering sweep as a base current, the reoxidation current detection voltage being a voltage that falls within the first voltage range and is higher than the first voltage, the electronic control unit is configured to make the exhaust gas as detected gas that does not contain sulfur oxides flow through the exhaust passage and to execute the boosting sweep and the lowering sweep, and the electronic control unit is configured to compute a difference between the base current and the output current, and is configured to use the difference as the parameter, the output current is a current that is obtained at the time point that the applied voltage becomes the reoxidation current detection voltage during the lowering sweep.

3. The control device for the gas detector according to claim 2, wherein the electronic control unit determines whether a magnitude of the difference is equal to or larger than a threshold difference, the electronic control unit determines that sulfur oxides in the specified concentration or higher are contained in the exhaust gas when the electronic control unit determines that the magnitude of the difference is equal to or larger than the threshold difference, and the electronic control unit is configured to determine that sulfur oxides in the specified concentration or higher are not contained in the exhaust gas when the electronic control unit determines that the magnitude of the difference is smaller than the threshold difference.

4. The gas detector according to claim 3, wherein the current detector is an ammeter.

5. The gas detector according to claim 2, wherein the current detector is an ammeter.

6. The control device for the gas detector according to claim 2, wherein the electronic control unit is configured to store a relationship between the difference and a concentration of sulfur oxides in the exhaust gas, and the electronic control unit is configured to detect the concentration of sulfur oxides in the exhaust gas based on the difference and the relationship.

7. The gas detector according to claim 6, wherein the current detector is an ammeter.

8. The control device for the gas detector according to claim 1, wherein the electronic control unit is configured to compute a minimum change amount and is configured to use the minimum change amount as the parameter, and the minimum change amount is a minimum value of a change amount of the output current, which is obtained by the electronic control unit, per specified elapsed time in a period in which the applied voltage falls within the first voltage range during the lowering sweep.

9. The control device for the gas detector according to claim 8, wherein the electronic control unit is configured to determine whether a magnitude of the minimum change amount is equal to or larger than a threshold minimum change amount, the electronic control unit is configured to determine that sulfur oxides in the specified concentration or higher are contained in the exhaust gas when the electronic control unit determines that the magnitude of the minimum change amount is equal to or larger than the threshold minimum change amount, and the electronic control unit is configured to determine that sulfur oxides in the specified concentration or higher are not contained in the exhaust gas when the electronic control unit determines that the magnitude of the minimum change amount is lower than the threshold minimum change amount.

10. The gas detector according to claim 9, wherein the current detector is an ammeter.

11. The gas detector according to claim 8, wherein the current detector is an ammeter.

12. The control device for the gas detector according to claim 8, wherein the electronic control unit is configured to store a relationship between the minimum change amount and a concentration of sulfur oxides in the exhaust gas and detects the concentration of sulfur oxides in the exhaust gas based on the minimum change amount and the relationship.

13. The gas detector according to claim 12, wherein the current detector is an ammeter.

14. The control device for the gas detector according to claim 1, wherein the electronic control unit is configured to set the applied voltage to an air-fuel ratio applied voltage by using the power supply circuit before executing one of the specified determination and the specified detection, the air-fuel ratio applied voltage being the applied voltage that is selected from a range where a limiting current of oxygen is generated, and the electronic control unit is configured to obtain the output current when the applied voltage is set as the air-fuel ratio applied voltage and to determine the first voltage and the second voltage based on one of an oxygen concentration in the exhaust gas and the air-fuel ratio of the air mixture supplied to the engine, the oxygen concentration being estimated based on the output current, and the air-fuel ratio of the air mixture being estimated based on the output current.

15. The gas detector according to claim 14, wherein the current detector is an ammeter.

16. The gas detector according to claim 1, wherein the current detector is an ammeter.

17. A control method for a gas detector, the gas detector including an element section, a power supply circuit, a current detector, and an electronic control unit, the element section including an electrochemical cell and a diffusion resistance body and being provided in an exhaust passage of an internal combustion engine, the electrochemical cell including a solid electrolyte body that has oxide ion conductivity, a first electrode and a second electrode, the first electrode and the second electrode being respectively provided on surfaces of the solid electrolyte body, the diffusion resistance body being constituted a porous material through which exhaust gas flowing through the exhaust passage is passable, the element section being configured that the exhaust gas flowing through the exhaust passage reaches the first electrode through the diffusion resistance body, the power supply circuit being configured to apply a voltage between the first electrode and the second electrode, and the current detector being configured to detect an output current that is a current flowing between the first electrode and the second electrode, the control method comprising:

controlling, by the electronic control unit, an applied voltage that is the voltage applied between the first electrode and the second electrode using the power supply circuit;

obtaining, by the electronic control unit, the output current using the current detector;

executing, by the electronic control unit, lowering sweep after executing boosting sweep using the power supply circuit when the electronic control unit determines that an air-fuel ratio of air mixture supplied to the internal combustion engine is in a stable state; and obtaining, by the electronic control unit, a specified parameter based on the output current and executing, by the electronic control unit, one of a specified determination and a specified detection based on the specified parameter, the boosting sweep being control to boost the applied voltage from a first voltage to a second voltage, the first voltage being selected from a first voltage range that is lower than a decomposition initiation voltage of sulfur oxides, and the second voltage being selected from a second voltage range that is higher than the decomposition initiation voltage of sulfur oxides, the lowering sweep being control to lower the applied voltage from the second voltage to the first voltage at a specified lowering rate, the specified determination being a determination on whether sulfur oxides in a specified concentration or higher are contained in the exhaust gas, the specified detection being detection of a concentration of the sulfur oxides in the exhaust gas, the specified parameter being a specified change, and correlated with a change occurred to the output current, the output current being increased as the concentration of the sulfur oxides contained in the exhaust gas is increased, the specified change being a change occurred to the output current due to the current that flows between the first electrode and the second electrode at a time when a reoxidation reaction of specified sulfur in the first electrode leads to generation of sulfur oxides, the specified sulfur being sulfur that is adsorbed to the first electrode at a time when the applied voltage becomes lower than the decomposition initiation voltage of sulfur oxides during the lowering sweep, the specified lowering rate being set to such a rate that a rate of the reoxidation reaction of the specified sulfur is rapidly increased at a time point at which the applied voltage becomes a voltage that falls within the first voltage range and also falls within a higher voltage range than the first voltage.

18. The control method for a gas detector according to claim 17, wherein the current detector is an ammeter.

* * * * *

UNITED STATES PATENT AND TRADEMARK OFFICE
CERTIFICATE OF CORRECTION

PATENT NO. : 10,712,323 B2
APPLICATION NO. : 15/796219
DATED : July 14, 2020
INVENTOR(S) : Keiichiro Aoki et al.

It is certified that error appears in the above-identified patent and that said Letters Patent is hereby corrected as shown below:

On the Title Page

In item (72), inventor 1, city, delete "Shizuoka-ken" and insert --Sunto-gun Shizuoka-ken--, therefor.

In item (72), inventor 2, city, delete "Okazaki" and insert --Okazaki-shi Aichi-ken--, therefor.

In item (72), inventor 3, city, delete "Susono" and insert --Susono-shi Shizuoka-ken--, therefor.

In item (72), inventor 4, city, delete "Susono" and insert --Susono-shi Shizuoka-ken--, therefor.

In the Specification

In Column 1, Line(s) 20, after "contained", delete "m" and insert --in--, therefor.

In Column 2, Line(s) 5, delete "is" and insert --in--, therefor.

In Column 3, Line(s) 13, delete "fells" and insert --falls--, therefor.

In Column 4, Line(s) 16, delete "may" and insert --may be--, therefor.

In Column 4, Line(s) 43, delete "Indicates" and insert --indicates--, therefor.

In Column 8, Line(s) 37, delete "28" and insert --20--, therefor.

In Column 11, Line(s) 59, after "show", delete "m" and insert --in--, therefor.

In Column 16, Line(s) 5, before "low", delete "g" and insert --a--, therefor.

In Column 18, Line(s) 4, delete "tipper" and insert --upper--, therefor.

Signed and Sealed this
Tenth Day of November, 2020

Andrei Iancu
*Director of the United States Patent and Trademark Office*

CERTIFICATE OF CORRECTION (continued)
U.S. Pat. No. 10,712,323 B2

In Column 18, Line(s) 5, after "region", insert --R--.

In Column 18, Line(s) 41, delete "compotes" and insert --computes--, therefor.

In Column 19, Line(s) 28, delete "18-232220" and insert --10-232220--, therefor.

In Column 23, Line(s) 49, delete "ether" and insert --other--, therefor.